United States Patent
De Almeida Barreto et al.

(10) Patent No.: US 12,178,401 B2
(45) Date of Patent: Dec. 31, 2024

(54) SYSTEMS AND METHODS FOR CHARACTERIZATION OF AN ENDOSCOPE AND AUTOMATIC CALIBRATION OF AN ENDOSCOPIC CAMERA SYSTEM

(71) Applicant: S&N ORION PRIME, S.A., Austin, TX (US)

(72) Inventors: João Pedro De Almeida Barreto, Coimbra (PT); Carolina Dos Santos Raposo, Coimbra (PT); Michel Goncalves Almeida Antunes, Coimbra (PT); Rui Jorge Melo Teixeira, Tondela (PT)

(73) Assignee: S&N ORION PRIME, S.A., Coimbra (PT)

( * ) Notice: Subject to any disclaimer, the term of this patent is extended or adjusted under 35 U.S.C. 154(b) by 257 days.

(21) Appl. No.: 17/762,179

(22) PCT Filed: Oct. 7, 2020

(86) PCT No.: PCT/US2020/054636
§ 371 (c)(1),
(2) Date: Mar. 21, 2022

(87) PCT Pub. No.: WO2021/071988
PCT Pub. Date: Apr. 15, 2021

(65) Prior Publication Data
US 2022/0392110 A1    Dec. 8, 2022

Related U.S. Application Data

(60) Provisional application No. 62/911,986, filed on Oct. 7, 2019, provisional application No. 62/911,950, filed on Oct. 7, 2019.

(51) Int. Cl.
A61B 1/00    (2006.01)
G06T 3/18    (2024.01)
(Continued)

(52) U.S. Cl.
CPC ...... *A61B 1/00179* (2013.01); *A61B 1/00009* (2013.01); *A61B 1/000094* (2022.02);
(Continued)

(58) Field of Classification Search
CPC ............ A61B 1/00179; A61B 1/00009; A61B 1/000094; A61B 1/000096; A61B 1/0005;
(Continued)

(56) References Cited

U.S. PATENT DOCUMENTS

| | | |
|---|---|---|
| 8,444,652 B2 | 5/2013 | Amis et al. |
| 9,438,897 B2 | 9/2016 | De Almeida Barreto et al. |

(Continued)

FOREIGN PATENT DOCUMENTS

| | | | |
|---|---|---|---|
| CN | 108938086 A | * | 12/2018 |
| WO | 2018232322 A1 | | 12/2018 |

(Continued)

OTHER PUBLICATIONS

International Patent Application No. PCT/US2022/041845 filed Aug. 29, 2022 listing Quist, Brian William as first Inventor, entitled, "Methods and Systems of Ligament Repair,", 108 pages.

(Continued)

*Primary Examiner* — Michael Lee
(74) *Attorney, Agent, or Firm* — Dickinson Wright PLLC

(57) ABSTRACT

Systems and methods for determining the calibration of an endoscopic camera consisting in a camera-head equipped with exchangeable, rotatable optics (the rigid endoscope), which is accomplished with no user intervention in the Operating Room by first characterizing the rigid endoscope through a set of parameters Φ and then using this lens descriptor Φ as input in a real-time software that processes the images acquired by an arbitrary camera-head equipped with the rigid endoscope, to provide the calibration of the complete endoscopic camera arrangement at every frame (Continued)

time instant, irrespective of the relative rotation of the lens scope with respect to camera-head or zoom settings. Also disclosed is an image software method that detects if the lens descriptor is not compatible with the rigid endoscope in use to prevent errors and warn the user about faulty situations.

12 Claims, 14 Drawing Sheets

(51) Int. Cl.
 G06T 7/13 (2017.01)
 G06T 7/33 (2017.01)
 G06T 7/80 (2017.01)
 G06T 15/20 (2011.01)

(52) U.S. Cl.
 CPC .......... *A61B 1/000096* (2022.02); *G06T 3/18* (2024.01); *G06T 7/13* (2017.01); *G06T 7/33* (2017.01); *G06T 7/80* (2017.01); *G06T 15/205* (2013.01); *G06T 2207/10* (2013.01); *G06T 2207/10068* (2013.01); *G06T 2210/41* (2013.01)

(58) Field of Classification Search
 CPC ... A61B 1/00183; A61B 1/00188; G06T 3/18; G06T 7/13; G06T 7/33; G06T 7/80; G06T 15/205; G06T 2207/10; G06T 2207/10068; G06T 2210/41; G02B 23/2484
 See application file for complete search history.

(56) References Cited

U.S. PATENT DOCUMENTS

| | | | |
|---|---|---|---|
| 9,526,587 | B2 | 12/2016 | Zhao et al. |
| 10,307,296 | B2 | 6/2019 | Tan et al. |
| 10,499,996 | B2 | 12/2019 | de Almeida Barreto |
| 2010/0168562 | A1 | 7/2010 | Zhao et al. |
| 2014/0285676 | A1* | 9/2014 | Barreto ............... H04N 17/002 |
| | | | 348/333.08 |
| 2015/0351967 | A1 | 12/2015 | Lim et al. |
| 2017/0046833 | A1* | 2/2017 | Lurie .................... G06T 17/20 |
| 2018/0071032 | A1 | 3/2018 | De Almeida Barreto et al. |
| 2018/0242823 | A1* | 8/2018 | Ichihashi ........... G02B 23/2461 |
| 2021/0145254 | A1* | 5/2021 | Shekhar ............ G02B 23/2453 |
| 2021/0161718 | A1 | 6/2021 | Ng et al. |
| 2022/0383588 | A1* | 12/2022 | De Almeida Barreto ................... |
| | | | A61B 1/00188 |

FOREIGN PATENT DOCUMENTS

| | | |
|---|---|---|
| WO | 2021071991 A1 | 4/2021 |
| WO | 2021168408 A1 | 8/2021 |
| WO | 2021203077 A1 | 10/2021 |
| WO | 2021203082 A1 | 10/2021 |
| WO | 2021257672 A1 | 12/2021 |
| WO | 2022006041 A1 | 1/2022 |
| WO | 2022006248 A1 | 1/2022 |
| WO | 2022159726 A1 | 7/2022 |

OTHER PUBLICATIONS

International Patent Application No. PCT/US2022/046857 filed Oct. 17, 2022 listing Torrie, Paul Alexander as first inventor, entitled, "Methods and Systems of Tracking Objects in Medical Procedures,", 77 pages.

International Search Report and Written Opinion of PCT/US2020/054636 mailed Mar. 10, 2021.

Melo, Rui, et al., "A New Solution for Camera Calibration and Real-Time Image Distortion Correction in Medical Endoscopy-Initial Technical Evaluation", IEEE Transactions on Biomedical Engineering, vol. 59, No. 3, Mar. 2012, pp. 634-644.

Yamaguchi, Tetsuzo, et al., "Development of a Camera Model and Calibration Procedure for Oblique-viewing Endoscopes," Computer Aided Surgery, vol. 9, No. 5, Feb. 2004, pp. 203-214.

Wu, C., et al., "A Full Geometric and Photometric Calibration Method for Oblique-viewing Endoscopes," Computer Aided Surgery, vol. 15, No. 1-3, Apr. 2010, pp. 19-31.

\* cited by examiner

* The rotation center Q is only estimated for the case of N > 1

$$\min_{f,\xi,O_0,Q,R_i^k,t_i^k} \sum_{k=0}^{K_0-1} r(\mathbf{x}_0^k, \mathbf{X}_0^k, R_0^k, t_0^k, f, \xi, O_0) +$$

$$+ \sum_{i=1}^{2} \sum_{k=0}^{K_i-1} r(\mathbf{x}_i^k, \mathbf{X}_i^k, R_i^k, t_i^k, f, \xi, R(\delta_i, Q)O_0)$$

SYSTEMS AND METHODS FOR CHARACTERIZATION OF AN ENDOSCOPE AND AUTOMATIC CALIBRATION OF AN ENDOSCOPIC CAMERA SYSTEM

CROSS-REFERENCE TO RELATED APPLICATIONS

This application is a 35 U.S.C. § 371 national phase of PCT International Application No. PCT/US2020/054636, filed Oct. 7, 2020, which claims priority to and the benefit of U.S. Provisional Patent Application No. 62/911,950, filed Oct. 7, 2019 ("'950 application") and U.S. Provisional Patent Application No. 62/911,986, filed on Oct. 7, 2019 ("'986 application"). All the noted applications are hereby incorporated herein by reference in their entireties for all purposes.

FIELD

The disclosure generally relates to the fields of computer vision and photogrammetry, and in particular, but not by way of limitation, the present disclosed embodiments are used in the context of clinical procedures of surgery and diagnosis for the purpose of calibrating endoscopic camera systems with exchangeable, rotatable optics (the rigid endoscope), identifying if a particular endoscope is being in use, or verifying it is correctly assembled to the camera head. These endoscopy systems are used in several medical domains, such as orthopedics (arthroscopy) or abdominal surgery (laparoscopy), and the camera calibration enables applications in Computer-Aided Surgery (CAS) and enhanced visualization.

BACKGROUND

Video-guided procedures, such as arthroscopy and laparoscopy, make use of a video camera equipped with a rigid endoscope to provide the surgeon with the possibility of visualizing the interior of the anatomical cavity of interest. The rigid endoscope, which, depending on the medical specialty, can be an arthroscope, laparoscope, neuroscope, etc., is combined with a camera comprising a camera-head and a Camera Control Unit (CCU), to form an endoscopic camera. These cameras are different from conventional ones mainly because of two characteristics. The first one is that the rigid endoscope, also referred to as lens scope or optics, is usually exchangeable for the sake of easy sterilization, with the endoscope being attached to the camera-head by the surgeon in the Operating Room (OR) before starting the medical procedure. This attachment is accomplished with a connector that allows the endoscopic lens to rotate with respect to the camera-head around its symmetry axis (the mechanical axis in FIG. 2), allowing the surgeon to change the direction of viewing without having to move the endoscopic camera in translation. The second distinctive characteristic of an endoscopic camera is that it usually contains a Field Stop Mask (FSM) somewhere along the image forwarding system that causes the acquired image to have meaningful content in a circular region which is surrounded by a black frame. The FSM usually contains a mark in the circular boundary whose purpose is to allow the surgeon to infer the down direction. This mark in the periphery of the circular image will be henceforth referred to as the notch (FIG. 2).

An important enabling step for computer-aided arthroscopy or laparoscopy is camera calibration such that 2D image information can be related with the 3D scene for the purpose of enhanced visualization, improved perception, measurement and/or navigation. The calibration of the camera system, that in this case comprises a camera-head equipped with a lens scope, consists in determining the parameters of a projection model that maps projection rays in 3D into points in pixel coordinates in the image, and vice-versa (FIG. 1). In the context of medical endoscopy, the applications of calibration are vast, ranging from distortion correction and rendering of virtual views for enhanced visualization, to surgical navigation, where the camera is used to measure 3D points and distances and the relevant information is typically overlaid with the patient's anatomy.

In endoscopic cameras with rotatable optics, the motion between the rigid endoscope and the camera sensor causes changes in the calibration parameters of the camera system which means that the projection model is not constant along time as it happens in conventional cameras. Since it is impractical to perform independent calibration for every possible position of the optics with respect to camera-head, the calibration parameters must be updated according to a camera model that accounts for this relative motion. Solutions for determining this relative rotation and updating the calibration accordingly have been proposed in the literature with examples including the use of a rotary encoder attached to the camera head [1], or the employment of an optical tracking system for determining the position of an optical marker attached to the scope cylinder [2]. These approaches present a serious drawback that is the need of additional equipment and instrumentation that is costly, occupies space in the OR, and disrupts the established surgical workflow.

U.S. Pat. No. 9,438,897 discloses a method to solve some of the aforementioned issues for accomplishing endoscopic camera calibration without requiring any additional instrumentation. The rotation of the lens scope is estimated at each frame time instant using image processing and the result is used as input into a model that, given the camera calibration at a particular angular position of the lens scope with respect to camera-head (the reference position), outputs the calibration at the current angular position. However, this method presents the following drawbacks: (i) calibration at the reference position requires the acquisition of one or more frames of a known checkerboard pattern (the calibration grid) in the OR, which, besides requiring user intervention, is typically a time-consuming process that must be performed with a sterile grid, and thus is undesirable and should be avoided, (ii) the disclosed method does not allow changes in the optical zoom during operation as it is not capable of updating the calibration parameters to different zoom levels, and (iii) it requires the lens scope to only rotate, and never translate, with respect to camera-head with the point where the mechanical axis intersects the image having to be explicitly determined.

The presently disclosed embodiments refer to a method that avoids the need of calibrating the endoscopic camera at a particular angular position in the OR after assembling the rigid scope in the camera head. This patent discloses models, methods and apparatuses for characterizing a rigid endoscope in a manner that enables to determine the calibration of any endoscopic camera system comprising the endoscope independently of the camera-head that is being used, the amount of zoom introduced by that camera-head, and the relative rotation or translation between the scope and the camera-head at a particular frame-time-instant. This allows the surgeon to change the endoscope and/or the camera-head during the surgical procedure and adjust the zoom as desired for better visualization of certain image contents without causing any disruption to the workflow of the procedure.

The present disclosure shows how to calibrate the rigid endoscope alone to obtain a set of parameters—the lens descriptor—that fully characterize the optics. The lens calibration is performed in advance (e.g. at the moment of manufacture) and the descriptor is then loaded into the Camera Control Unit (CCU) to be used as input in a real-time software that automatically provides the calibration of the complete endoscopic camera arrangement, comprising both camera-head and lens, at every frame instant, irrespective of the relative rotation between the two components. This is accomplished in a seamless manner to the user.

Since this descriptor characterizes a lens or a batch of lenses, it can also be used for the purposes of identification and quality control. Thus, and building on this functionality, it is also disclosed a method for detecting inconsistencies between the lens descriptor loaded in the CCU and the actual rigid endoscope assembled in the camera-head. This method is useful to warn the user if the lens being used is not the correct one and/or if it is damaged or has not been properly assembled in the camera-head.

The present disclosure can be used in particular, but not by way of limitation, in conjunction with the methods disclosed in U.S. Pat. No. 9,438,897 to correct image radial distortion and enhance visual perception, or with the methods disclosed in US 20180071032 A1 to provide guidance and navigation during arthroscopy, for the purpose of accomplishing camera calibration at every frame time instant, which is a requirement for those methods to work.

SUMMARY

Systems, methods and apparatuses for determining the calibration of an endoscopic camera consisting in a camera-head equipped with exchangeable, rotatable optics (the rigid endoscope), such that 2D image points can be related with 3D projection rays in applications of computer-aided surgery, and where the rigid endoscope is characterized in advance (e.g. in factory at manufacture time) to accomplish camera calibration without requiring any user intervention in the Operating Room (OR).

A method for characterizing a rigid endoscope through a set of parameters $\phi$ that are then used as input in a real-time software that processes the images acquired by an arbitrary camera-head equipped with the rigid endoscope to provide the calibration of the complete endoscopic camera arrangement at every frame time instant, irrespective of the relative rotation between the lens scope and the camera-head or zoom settings.

An image software method detects if the lens descriptor $\phi$ is not compatible with the rigid endoscope in use, which is useful to prevent errors and warn the user about faulty situations such as usage of the incorrect lens, defects in the lens or camera-head or improper assembly of the lens in the camera-head.

BRIEF DESCRIPTION OF THE DRAWING

For a more complete understanding of the present disclosure, reference is made to the following detailed description of exemplary embodiments considered in conjunction with the accompanying drawings.

DETAILED DESCRIPTION

It should be understood that, although an illustrative implementation of one or more embodiments is provided below, the various specific embodiments may be implemented using any number of techniques known by persons of ordinary skill in the art. The disclosure should in no way be limited to the illustrative embodiments, drawings, and/or techniques illustrated below, including the exemplary designs and implementations illustrated and described herein. Furthermore, the disclosure may be modified within the scope of the appended claims along with their full scope of equivalents.

In this patent, 2D and 3D vectors are written in bold lower and upper case letters, respectively. Functions are represented by lower case italic letters, and angles by lower case Greek letters. Points and other geometric entities in the plane are represented in homogeneous coordinates, as it is commonly done in projective geometry, with 2D linear transformations in the plane being represented by 3×3 matrices and equality being up to scale. In addition, throughout the text different sections are referenced by the numbers of their paragraphs using the symbol §.

1. Camera Model for Endoscopic Systems with Exchangeable, Rotatable Optics (the Rigid Endoscope)

Figure 1:
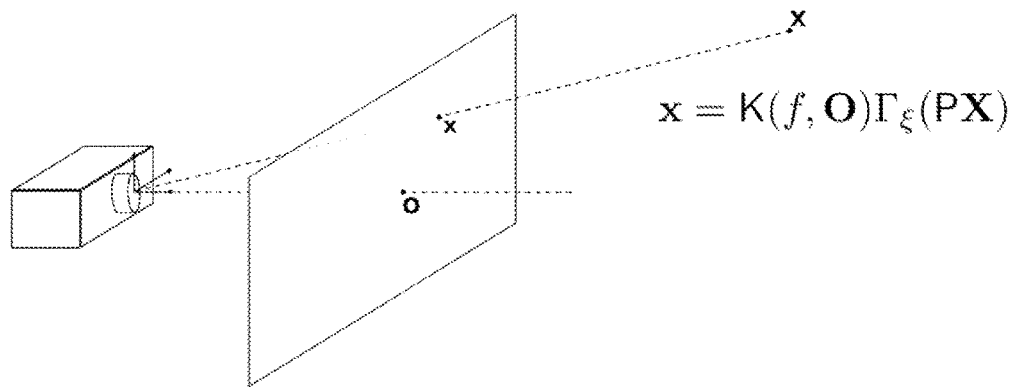
FIG. 1 is an embodiment of a camera projection model depicting the mapping of a projection ray, that is defined by 3D point X in the scene and the projection center of the camera, onto a 2D point x in pixel coordinates in the image plane. The model can be seen as a composition of a projection P according to the pin-hole model that maps the 3D point X onto 2D, a function $\Gamma$ that accounts for the non-linear effect of radial distortion introduced by the optics that is quantified by $\xi$, and the intrinsic parameters of the camera K(f, O) that depend on the focal length f and principal point O where the optical axis is projected onto the image.

Camera calibration is the process of determining the camera model that projects 3D points X in the camera reference frame into 2D image points x in pixel coordinates. Alternatively, the camera model can be interpreted as the function that back-projects image points x into light rays going through the 3D point X in the scene. This process is illustrated in FIG. 1. Camera calibration is a key component in many applications, ranging from visual odometry to 3D reconstruction, and also including the removal of image artifacts for enhanced visual perception such as radial distortion.

Conventional, commonly used cameras are described by the so-called pin-hole model that can be augmented with a radial distortion model that accounts for non-linear effects introduced by small optics and/or fish-eye lenses. In this case, points X in the scene are projected onto points x in the image according to the formula $x = K \Gamma_\xi(PX)$ where x and X are represented in homogeneous coordinates with the equality being up to scale, $P = [I \ 0_{3 \times 1}]$ is a 3×4 projection matrix with I denoting the 3×3 identity matrix, K is the so-called matrix of intrinsic parameters with dimension 3×3, and $\Gamma$ denotes a distortion function with parameters $\xi$. Henceforth, and without loss of generality, it will be assumed that the camera is skewless with unitary aspect ratio, yielding a model that approximates well the majority of modern cameras where the deviation of the skew from zero and of the aspect ratio from one is negligible. With this assumption, K depends solely on the focal length f and image coordinates of the principal point $O=[O_x, O_y, 1]^T$ such that $$K(f, O) = \begin{bmatrix} f & 0 & O_x \\ 0 & f & O_y \\ 0 & 0 & 1 \end{bmatrix}.$$

The distortion function $\Gamma$ represents a mapping in 2D and can be any of the many distortion functions or models available in the literature that include, but are not limited to, the polynomial model (also known as Brown's model), the division model, the rational model, the fish-eye lens model, etc., in either its first order or higher order (multi-parameter) versions with $\xi$ respectively being a scalar or a vector.

Figure 2:
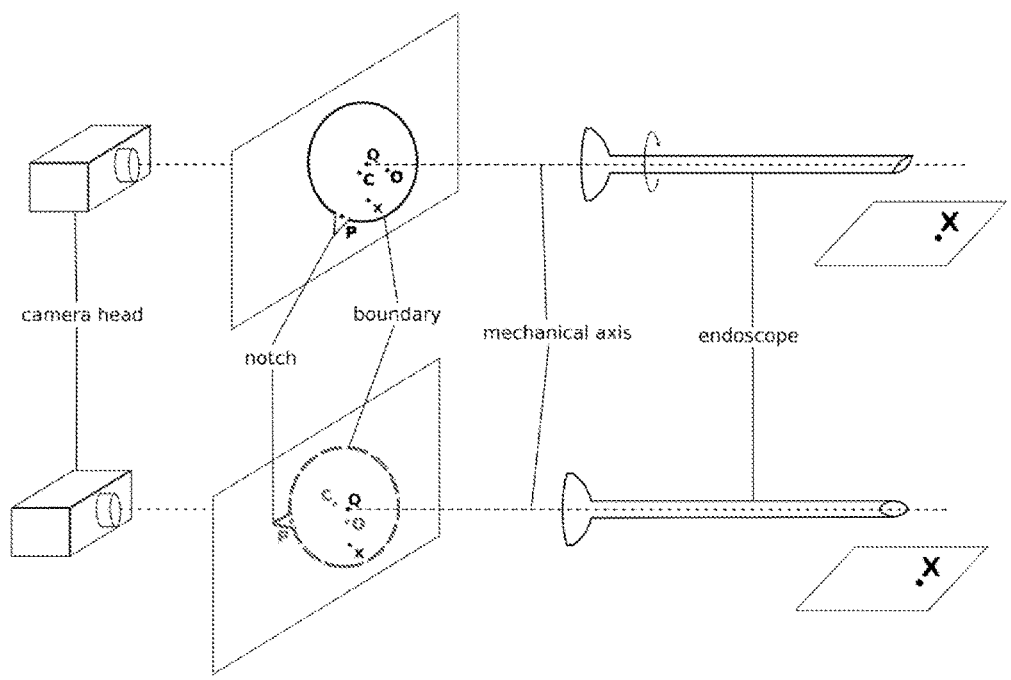
FIG. 2 shows exemplary embodiments of the image formed by an endoscopic camera with exchangeable, rotatable optics (the rigid endoscope). The lens is cylindrical shaped and rotates around its longitudinal, symmetry axis, henceforth referred to as the mechanical axis, that intersects the image plane in the rotation center Q. The rigid endoscope has a Field Stop Mask (FSM) somewhere along the image forwarding system that is projected onto the image plane as a black frame around a circle $\Omega$ with center C (the circular boundary) that contains the meaningful visual contents (refer to FIG. 3 for an illustration). The image boundary typically has a mark in an image point P, henceforth referred to as the notch, that allows the surgeon to infer the rotation between scope and camera-head. If the scope rotates around the mechanical axis with respect to the camera-head by an angle $\delta$, then the circle center C, notch P and principal point O also rotate by that same amount $\delta$, around Q.
Figure 2:
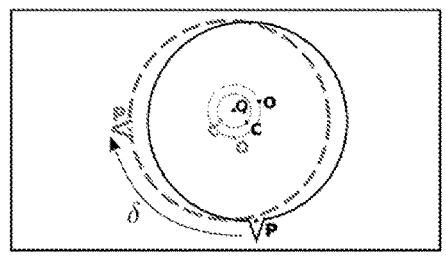

An endoscopic camera, that results from combining a rigid endoscope with a camera, has exchangeable optics for the purpose of easy sterilization, with the endoscope having in the proximal end an ocular lens (or eye-piece) that is assembled to the camera using a connector that typically allows the surgeon to rotate the scope with respect to the camera-head. As illustrated in FIG. 2, this rotation is performed around a longitudinal axis of the endoscope (the mechanical axis) that intersects the image plane in point Q. The Field Stop Mask (FSM) in the lens scope projects onto the image plane as a black frame around a region with visual content that has a circular boundary $\Omega$ with center C and a notch P.

The mechanical axis is roughly coincident with the symmetry axis of the eye-piece that does not necessarily have to be aligned with the symmetry axis of the cylindrical scope and/or pass through the center of the circular region defined by the FSM. These alignments are aimed but never perfectly achieved because of mechanical tolerances in building and manufacturing the endoscope. Thus, the rotation center Q, the center of the circular boundary C and the principal point O are in general distinct points in the image, which complicates camera modeling but, and as disclosed ahead, can be used as a signature to identify a particular endoscope or batch of similar endoscopes.

Consider that the endoscopic camera is calibrated for a certain position of the scope, such that K(f, O) is the matrix of intrinsic parameters and $\xi$ is the distortion parameter quantifying radial distortion according to a chosen model $\Gamma$ (FIG. 1). If the scope undergoes a rotation by an angle $\delta$ with respect to the camera head, the distortion $\xi$ and focal length f remain unchanged, but the principal point O rotates by the same amount $\delta$ around Q (FIG. 2). This causes the matrix of intrinsic parameters to become K(f, R($\delta$, Q) O), where R($\delta$, Q) is a 3×3 matrix representing a 2D rotation in image around point $Q=[Q_x, Q_y, 1]^T$ by an angle $\delta$.

Similarly to causing a rotation in the principal point O, such that it becomes O'=R($\delta$, Q) O, the rotation of the scope with respect to the camera head causes circle $\Omega$ with center C and notch P to become circle $\Omega'$ with center C'=R($\delta$, Q)C and notch P'=R($\delta$, Q)P (FIG. 2).

2. Calibration of an Endoscopic Camera with Exchangeable, Rotatable Optics

Summarizing, in order to obtain the correct calibration parameters of an endoscopic camera at all times, the focal length f, distortion $\xi$, and principal point O must be known for a particular rotation angle between camera-head and lens scope (the reference angular position) and the location of the principal point must be updated during operation according to O'=R($\delta$, Q)O, which requires knowing the rotation center Q and the angular displacement $\delta$ between current and reference angular positions at every frame time instant.

Figure 7:
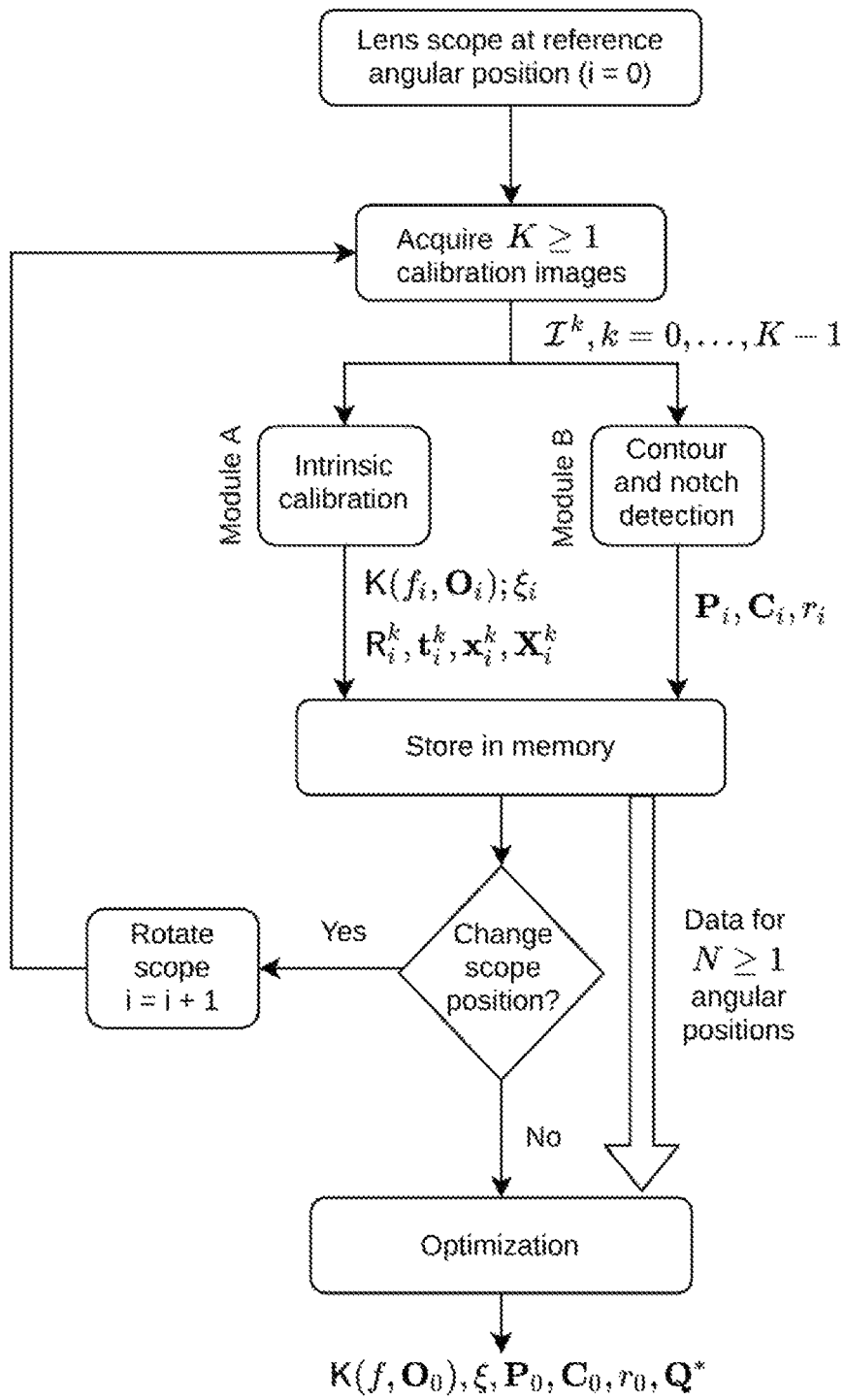
FIG. 7 shows the sequence of steps for obtaining the camera calibration at the reference position i=0. With the lens scope at the reference angular position, the user starts by acquiring K≥1 calibration images. Intrinsic camera calibration is then performed as well as the detection of the circular boundary and notch. This data is stored in memory, giving the user the possibility to change the position of the lens scope and repeating the above steps N times. A final optimization scheme that minimizes the re-projection error for all calibration images simultaneously is then performed.

The calibration of the endoscopic camera at the reference angular position, which can be easily recognized by the position P of the notch, can be performed "off-line" before starting the clinical procedure by following the steps of FIG. 7. The determination of f, $\xi$ and O requires the use of an intrinsic camera calibration method (Module A in FIG. 7) that receives as input one or more frames acquired at reference position P (or $P_0$) as described in §§ [0045]-[0049]. If the objective is to also determine the rotation center Q, then input frames must be acquired in additional angular positions $P_i$ with i=1, ..., N, where these frames can be used to improve the accuracy in determining f, $\xi$ and O at the reference angular position $P_0$ as disclosed in §§ [0065]-[0069].

Figure 9:
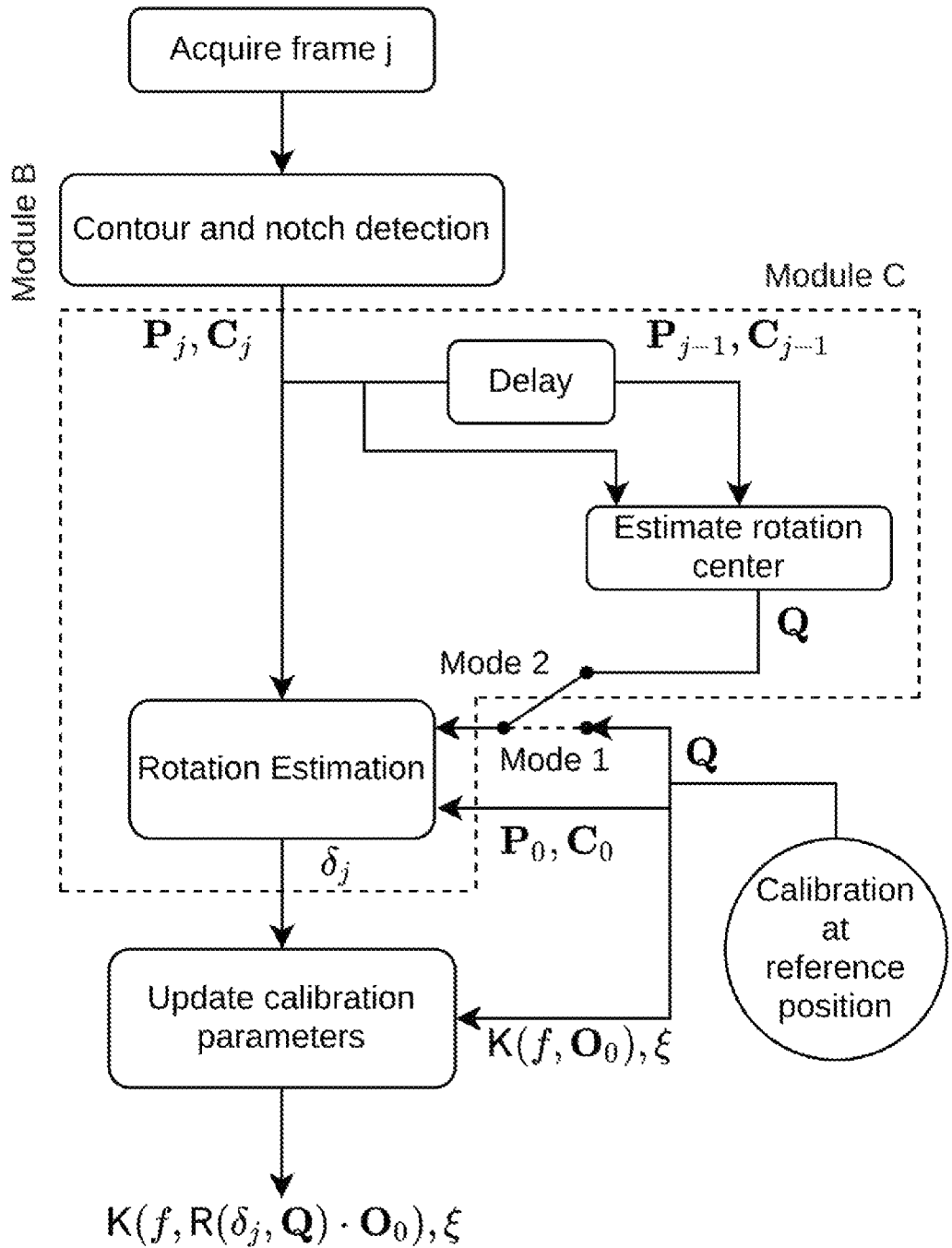
FIG. 9 shows the sequence of steps of the online update of the calibration parameters. Every time a new frame j is acquired, the circular boundary and notch are detected and the angular displacement is computed using an estimate of the rotation center Q which is obtained either from the offline calibration result (Mode 1) or by estimation from successive frames (Mode 2). As a final step, the calibration parameters are updated.

The update of the camera model is carried "on-line" during the clinical procedure at every frame time instant by following the steps of FIG. 9 that are further disclosed in §§ [0070]-[0072]. The angular displacement $\delta$ can be determined from a multitude of methods, either using additional instrumentation, such as optical encoders [1] or optical tracking [2], or exclusively relying on image processing. The disclosed embodiments will consider, without loss of generality, that the relative rotation between the lens scope and the camera-head is determined using an image processing method that is also disclosed. This method detects and estimates the position of the boundary contour $\Omega_i$ with center $C_i$ and notch $P_i$ in every frame i (Module B in FIG. 9 further disclosed in §§ [0050]-[0057]), and then infers the corresponding angular displacement $\delta$ with respect to reference position with, or without, prior knowledge of the rotation center Q (Module C in FIG. 9 further disclosed in §§ [0058]-[0064]).

2.1 Camera Calibration at a Particular Angular Position Including Intrinsics K(f, O) and Distortion $\xi$ (Module A in FIG. 7)

The literature is vast in methods for calibrating a pinhole camera with radial distortion which can be divided into two large groups: explicit methods and auto-calibration methods. The former use images of a known calibration object, which can be a general 3D object, a set of spheres, a planar checkerboard pattern, etc., while the latter rely on correspondences across successive frames of unknown, natural scenes. The two approaches can require more or less user supervision, ranging from manual to fully automatic depending on the particular method and underlying algorithms.

The disclosed embodiments will consider, without loss of generality, that the camera calibration at a particular angular position of the lens scope with respect to camera-head will be conducted using an explicit method that makes use of a known calibration object such as a planar checkerboard pattern or any other planar pattern that enables to establish point correspondences between image and calibration object. This approach is advantageous with respect to most competing methods because of the good performance in terms of robustness and accuracy, the ease of fabrication of the calibration object (planar grid), and the possibility of accomplishing full calibration from a single image of the rig acquired from an arbitrary position. However, other explicit or auto-calibration methods can be employed to estimate the focal length f, distortion and principal point O of the endoscopic camera for a particular relative rotation between camera-head and endoscope (the reference angular position).

The explicit calibration using a planar checkerboard pattern typically comprises the following steps: acquisition of a frame of the calibration object from an arbitrary position or 3D pose (rotation R and translation t of the object with respect to camera); employment of image processing algorithms for establishing point correspondences x, X between image and calibration object; execution of a suitable calibration algorithm that uses the point correspondences for the estimation of the focal length f, the principal point O and distortion parameters $\xi$, as well as the pose R, t of the object with respect to the camera.

The approach can be applied to multiple calibration frames $I^k$, k=0, ..., K−1, instead of a single one, for the purpose of improving robustness and accuracy. In this case the calibration is independently carried for each frame and a last optimization step that minimizes the re-projection error is used to enforce the same intrinsic parameters K(f, O) and distortion across the multiple frames, while considering a different pose $R^k$, $t^k$ for each frame.

2.2 Detection of the Circular Boundary and Notch (Module B in FIG. 7 and FIG. 9)

Figure 3A:
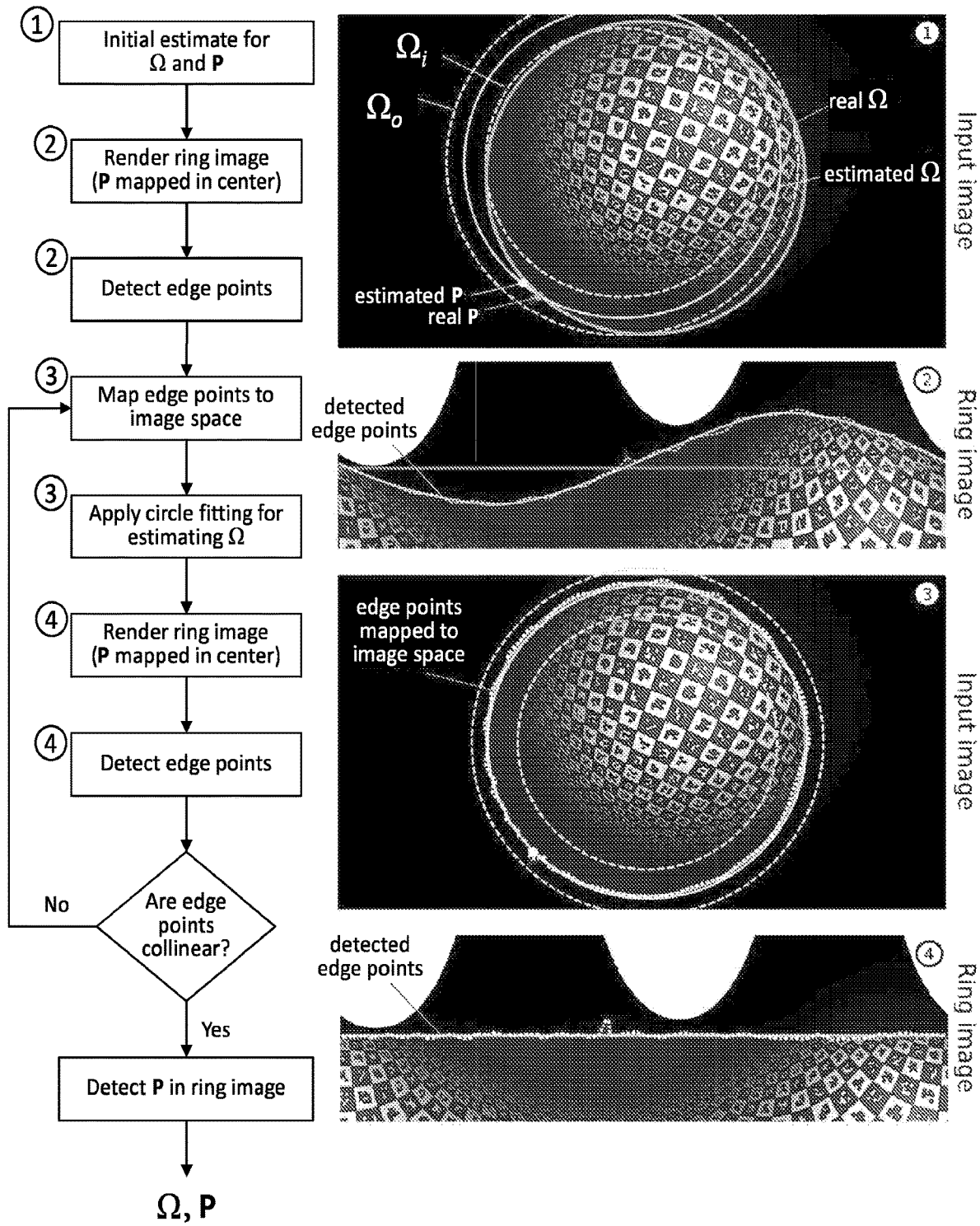
FIG. 3A shows the sequence of steps for detecting the circular boundary C and notch P at each frame time instant. Starting with an initial estimate for the boundary $\Omega$ and notch P, the algorithm comprises rendering a ring image having P mapped in the center (step 1), detecting edge points on that ring image (step 2), and iterating through the following steps until the stopping criterion is met: mapping the edge points back to the image space for the estimation of a boundary circle proposal (step 3), and rendering a new ring image for detecting more accurate edge points (step 4). This cycle stops when the edge points in the ring image are collinear. The final step consists in detecting the notch P in the ring image using a correlation-based strategy with a known notch template. The detected boundary $\Omega$ and notch P will be used as initialization in the following frame time instant.

The circular boundary and the notch of the FSM can be detected as schematized in FIG. 3A. The method starts by considering an initialization for the boundary $\Omega$ and notch P, which are used as input to a warping function that renders the so-called ring image. The initialization for the boundary $\Omega$ and notch P can be obtained from a multitude of methods which include, but are not limited to, deep/machine learning, image processing, statistical-based and random approaches. Exemplifying, and regarding the boundary Q, it can be initialized by considering a circle centered in the image center and with a radius equal to half the minimum between the width and the height of the image, by radially searching for the transition between the image's black frame and the region containing meaningful information, or by using a deep learning frame work for detecting circles, generic conics, or any other desired shape. Concerning the notch P, it can be initialized in a random location on the boundary or by using learning schemes and/or image processing for detecting the known shape of the notch. Referring to steps 1 and 2 of FIG. 3A, the ring image is obtained by considering an inner circle $\Omega_i$ and an outer circle $\Omega_o$ centered at C of $\Omega$ that have radii $r_i$<r and $r_o$>r, respectively, where r is the radius of Q. An uniform spacing between $r_i$ and $r_o$ defines a set of concentric circles $\Omega_j$. For each $\Omega_j$, the image signal is interpolated and concatenated. The hypothesized notch P is mapped in the center of the ring image.

Figure 3B:
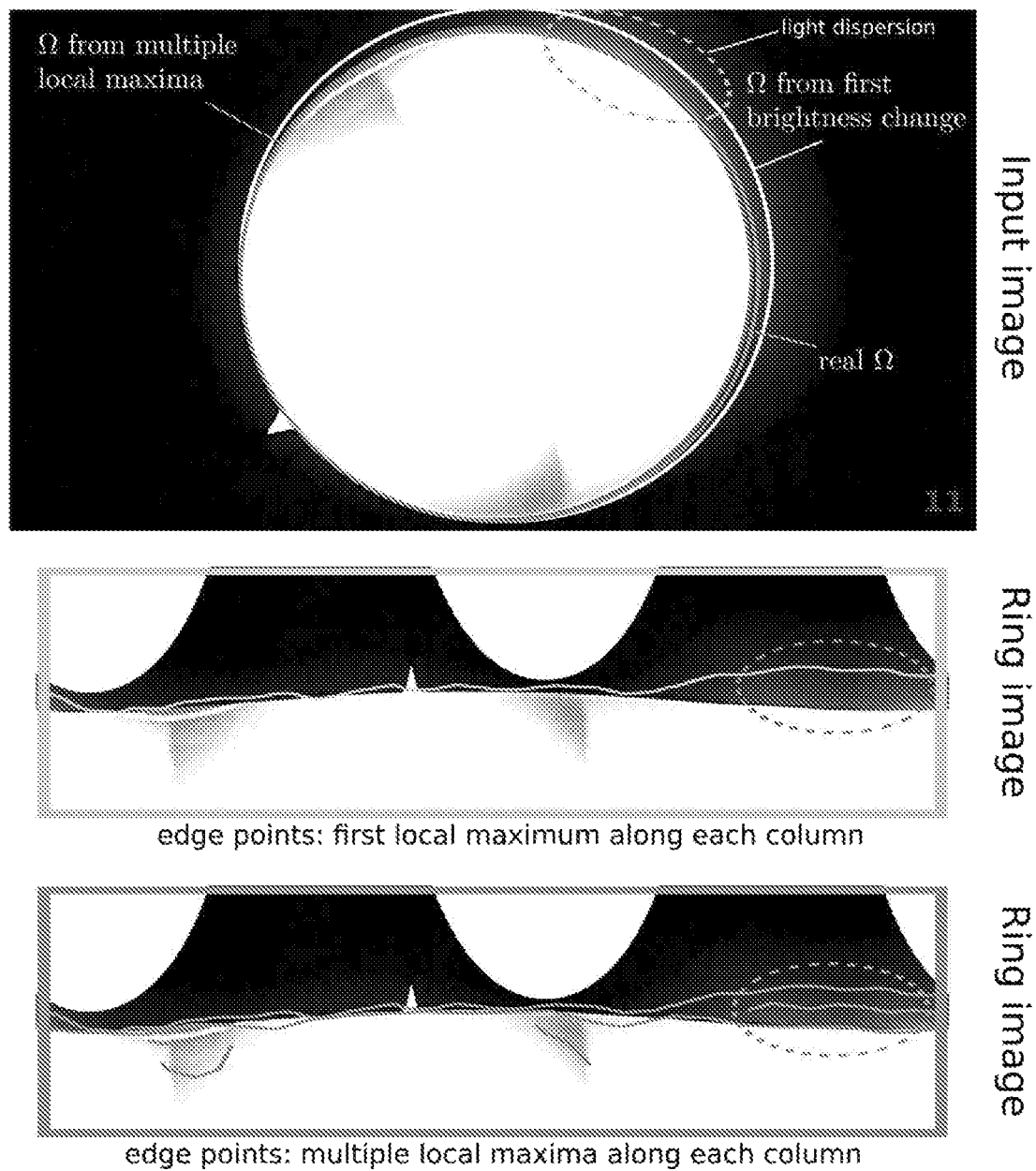
FIG. 3B illustrates the advantage of detecting multiple edge points for each ring image column. In case of strong light dispersion (dashed ellipse), the edge points (red points) corresponding to the first local maxima along each column of the ring image do not always correspond to the correct image boundary, and the circle boundary estimation fails (yellow circle). This is solved by detecting multiple local maxima for each column of the ring image, and using these edge points as input to a robust circle estimation scheme (green circle).

Referring to step 2 of FIG. 3A, the edge points on the ring image, which theoretically correspond to points that belong to the boundary, are detected by searching for sharp brightness changes along the direction from the periphery towards the boundary center. This is achieved by analyzing the magnitude of the 1-D spatial derivative response (gradient magnitude) along each column of the ring image. A possible solution for selecting these edge points would be to pick the first local maximum of the gradient magnitude for each column. However, and as depicted in FIG. 3B, there are situations in which this approach fails (e.g. situations of strong light dispersion near the boundary). In order to overcome this, for each column of the ring image, a set of M edge points corresponding to local maxima of the gradient magnitude are selected.

Then, the detected edge points are mapped back to the Cartesian image space so that the circle boundary can be estimated. This is performed using a circle fitting approach inside a robust framework. Given a set of noisy data points, which can be contaminated by outliers, the objective of circle fitting is to find a circle that minimizes or maximizes a particular error or cost function that quantifies how well a given circle fits the data points. The most widely used techniques either minimize the geometric or the algebraic (approximate) distances from the circle to the data points. In order to handle outlier data points, a robust framework such as RANSAC is usually employed. The steps of ring image rendering, detection of edge points and robust circle estimation are performed iteratively until the detected edge points are collinear, in a robust manner. If this occurs, the algorithm proceeds to the detection of the notch P by performing correlation with a known template of the notch. The output of this algorithm is the notch location P and the circle $\Omega$ with center C and radius r.

Figure 3C:
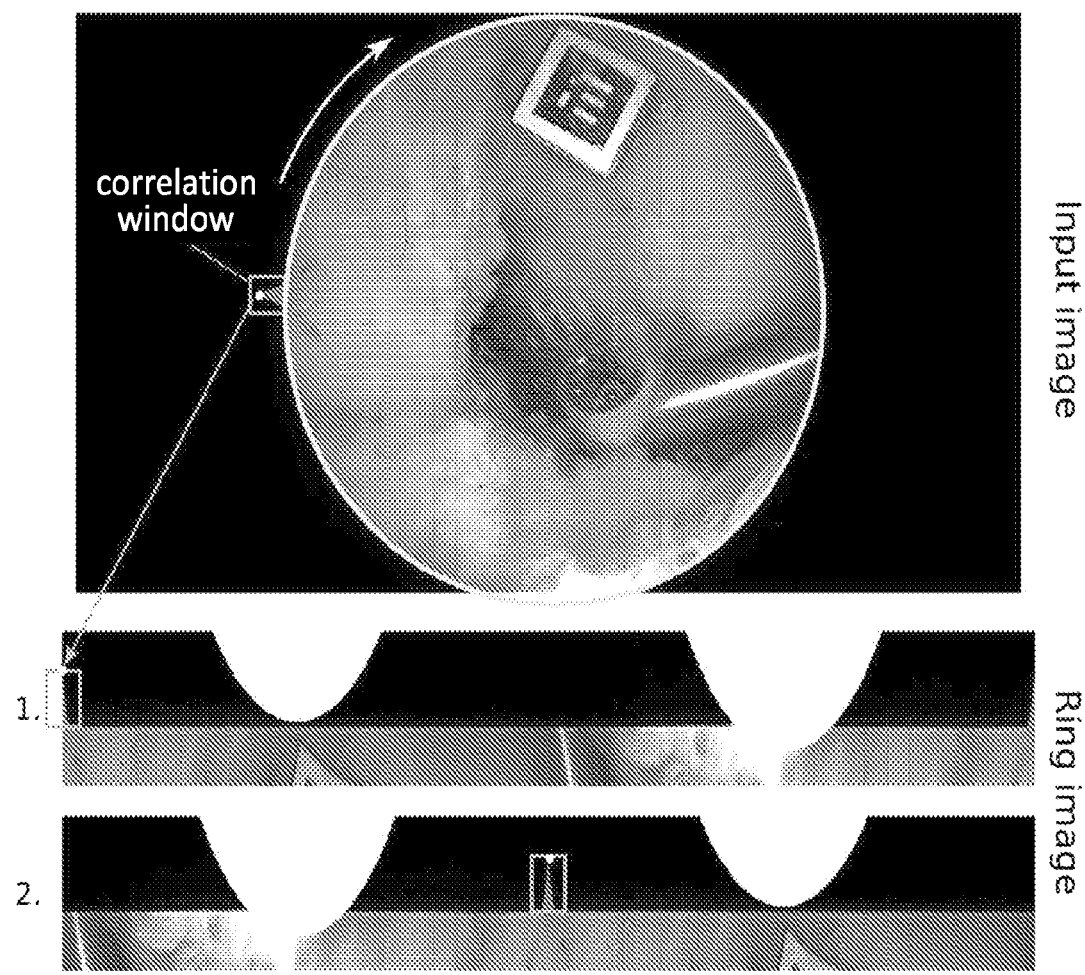
FIG. 3C illustrates the strategy used for solving the issue of generating ring images in which the lens notch region is not contiguous. (Step 1) A fixed angular position (arrow) for the beginning of the ring image can cause notch P to be partially cut. (Step 2) The issue of step 1. can be solved by centering the ring image using an initial estimate of the lens notch P.

As depicted in FIG. 3C, by centering the ring image using an initial estimation of the notch location P, it is guaranteed that the image part corresponding to the notch is contiguous, enabling its detection at all times. Moreover, the collinearity of the edge points is chosen as the stopping criterion because the edge points belong to a straight line if and only if the estimated boundary is perfectly concentric with the real boundary.

Figure 3D:
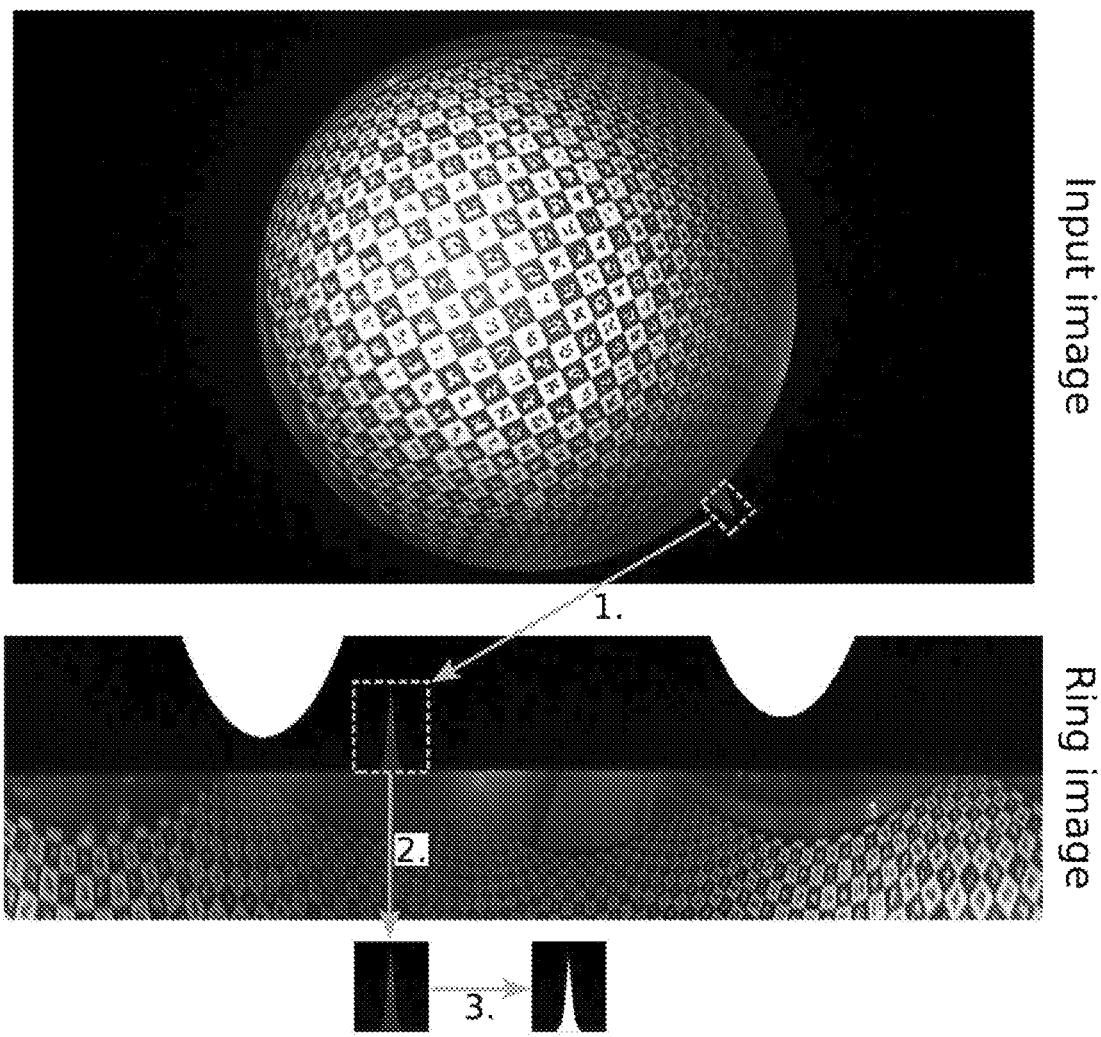
FIG. 3D shows the strategy for obtaining a lens specific notch template. At calibration time, and after generating the ring image (step 1), a specific region around the lens notch location P is extracted (dashed rectangle of step 2). Then, an adaptive binarization strategy is employed for generating a notch template composed of a bright triangular shape with a dark rectangular background (step 3).

As shown in FIG. 3D, a lens specific notch template is extracted at calibration time, which is usually composed by a bright triangle and a dark rectangular background.

The disclosed method for boundary and notch detection can have other applications such as the detection of engravings in the FSM for reading relevant information including, but not limited to, particular characteristics of the lens.

In addition, although the implementation of this method assumes that the boundary can be accurately represented by a circle, generic conic fitting can be used in the method without major modifications.

2.3 Image-Based Measurement of the Relative Rotation Between Endoscope and Camera-Head (Module C in FIG. 9)

As previously mentioned, finding the calibration for current frame i can be accomplished by rotating the principal point O (or $O_0$) at the reference angular position by angle $\delta_i$ around the rotation center Q. In this case, both center Q and the angular displacement $\delta_i$ between frame i and frame 0 corresponding to the reference position must be estimated.

Figure 4A:
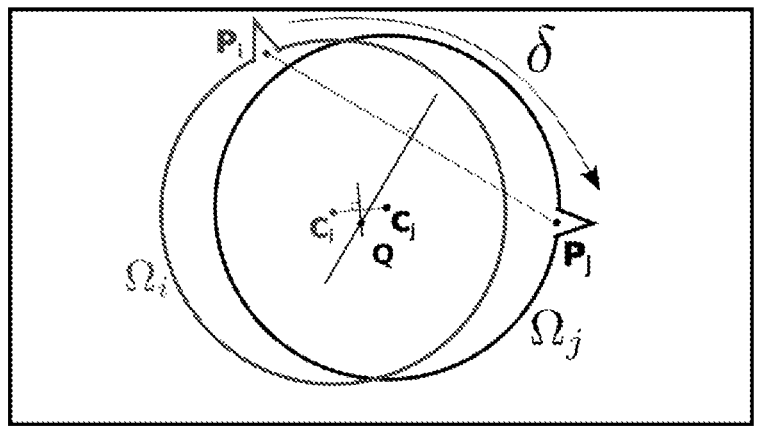
FIG. 4A illustrates the estimation of the rotation center Q from two frames in which the notches $P_i$, $P_j$ have been detected. Q is estimated by simply intersecting the bisectors of segments $\overline{C_iC_j}$ and $\overline{P_iP_j}$, where $C_i$, $C_j$ are the centers of the boundaries detected in both frames.
Figure 4B:
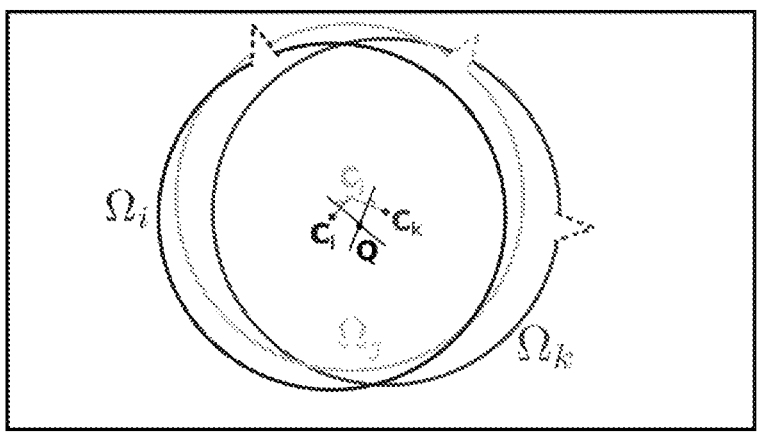
FIG. 4B illustrates the estimation of the rotation center Q from three frames by making use solely of the centers $C_i$, $C_j$, $C_k$ of the boundaries detected in these frames. Q is the intersection of the bisectors of segments $\overline{C_iC_j}$ and $\overline{C_jC_k}$.

FIG. 4A depicts the process of estimating Q from two frames i and j acquired at two different angular positions. This is performed by simply intersecting the bisectors of the line segments whose endpoints are respectively the centers $C_i$, $C_j$ and the notches $P_i$, $P_j$ that are determined by applying the steps of FIG. 3 to each frame. If the notches cannot be detected in the images, due to occlusions, poor lighting, over-exposure with light dispersion, etc., then it is possible to estimate Q using solely the centers of the circular boundaries detected in three frames acquired at different angular positions. This process is illustrated in FIG. 4B, where it can be seen that Q is the intersection of the line segments obtained by joining the centers of the boundaries detected in frames i, j and k.

If the rotation center Q is known and the center and notch at the reference angular position are respectively $C_0$ and $P_0$, then the angular displacement $\delta_i$ can be inferred from the notch $P_i$, the boundary center $C_i$, or both simultaneously ($\delta_i = \sphericalangle P_0QP_i = \sphericalangle C_0QC_i$), with their positions being determined by applying the steps of FIG. 3 to the current frame i. If notch P is not visible, $\delta_i$ can be determined from $C_0$, $C_i$.

Figure 5:
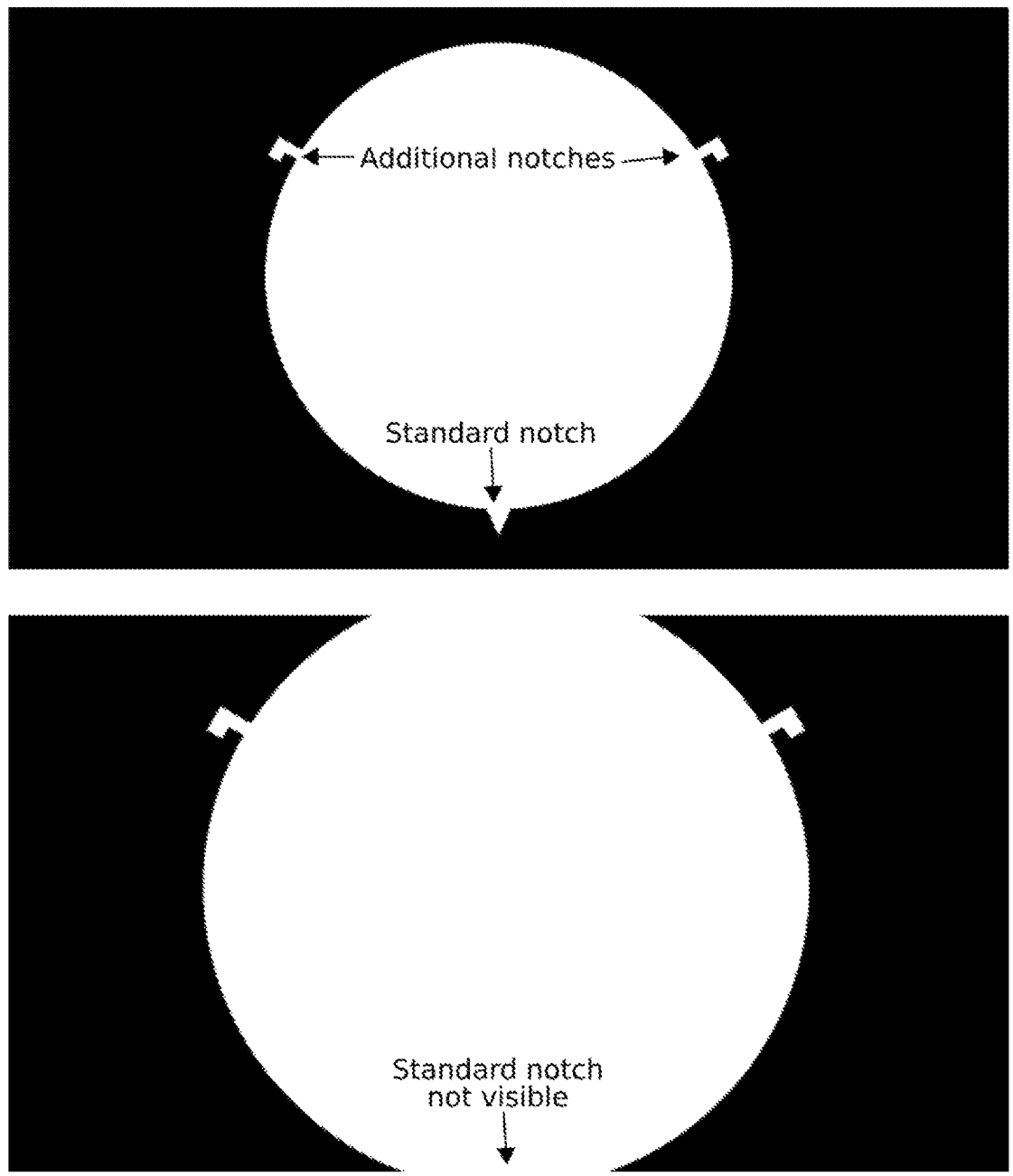
FIG. 5 illustrates an embodiment of a Field Stop Mask (FSM) containing multiple marks with different shapes so that they can be uniquely identified. The objective is to have redundancy to improve the accuracy of rotation estimation and be resilient to situations where the circular boundary is partially projected beyond the frame limits and a single notch might not be visible at all times, precluding or hampering estimation.
Figure 6:
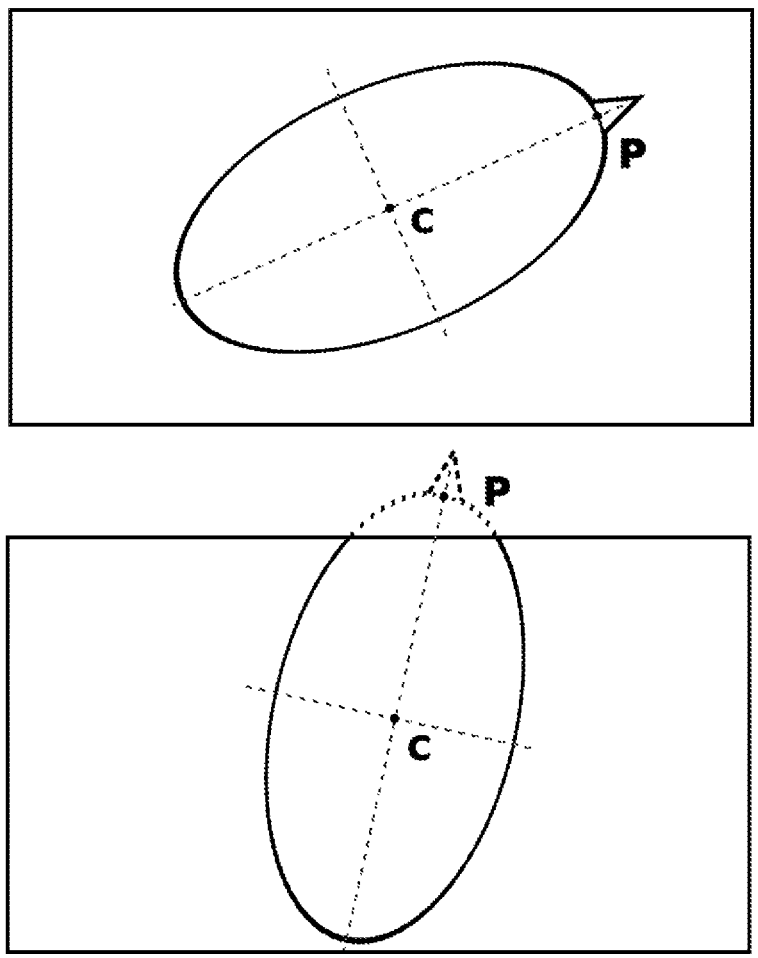
FIG. 6 illustrates an embodiment of a Field Stop Mask (FSM) having an elliptic shape such that its lack of circular symmetry allows the location of the notch P to be inferred at all times.

Since the distance from the rotation center Q to the notch P is significantly larger than that between Q and C, estimations using the notch P are in general more robust and accurate, and thus it is important that it can be detected in all frames. Since its detection is mostly affected by situations of occlusion, one solution is to consider multiple notches in the FSM to ensure that at least one is always visible in the frame. FIG. 5 presents one exemplary FSM containing multiple marks with different shapes, allowing their identification, with one of these marks being used as the point of reference or standard notch P. An alternative solution is to consider an FSM that projects onto a black frame that renders an image boundary with a shape that does not have circular symmetry, in which case this lack of circular symmetry of the detected shape can be used to infer the location of a notch or point of reference P that is not visible. FIG. 6 presents one exemplary FSM that renders an elliptic shaped boundary with the major axis going through the notch P which enables to infer its position at all times.

The algorithm described in §§ [0050]-[0057] for detecting the notch can be extended to the case when the FSM contains multiple notches. For this, the last step in FIG. 3A is modified by determining the correlation signal for each notch independently, fusing all signals together using the known relative location of the notches and finding the point of highest correlation. With this approach it is guaranteed that at least one notch is detected, even if one or more of them are occluded.

Without loss of generality, it is assumed in the remainder of this patent that the FSM has only one notch P that is always visible and the rotation center Q is determined from two frames.

Whenever more than two frames acquired at different angular positions are available, and in order to filter out possible noisy estimations of the rotation center Q and the relative rotation $\delta_i$, a filtering approach can be applied. The filter can take as input the previous estimation for Q and the current boundary and notch and output the updated location of Q and an estimation for the relative rotation $\delta_i$. This filtering technique can be implemented using any temporal filter such as a Kalman filter or an Extended Kalman filter.

2.4 Offline Calibration at the Reference Angular Position

Figure 8:
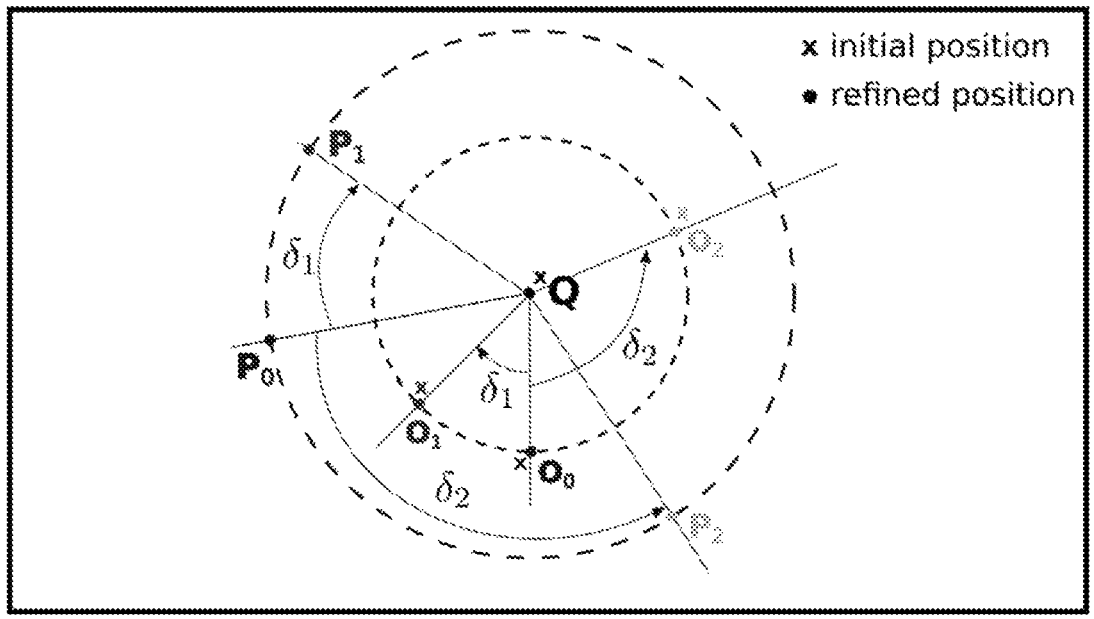
FIG. 8 illustrates the optimization scheme employed when the calibration images are acquired at N>1 angular positions i of the scope with i=0 being the reference position and i=1, . . . , N-1 being the additional positions. This optimization step enforces the rotation model of the scope, which is a plane rotation of angle $\delta_i$ around the rotation center Q that transforms the principal point $O_0$ and notch $P_0$ into points $O_i$ and $P_i$, respectively. The optimization scheme serves to estimate the calibration parameters at the reference position, while minimizing the re-projection error in all acquired calibration images and enforcing this model for the scope rotation for all sampled angular positions simultaneously. An initialization for the rotation center Q may be obtained from the method schematized in FIG. 7.

FIG. 7 gives a schematic description of the procedure for obtaining the camera calibration at reference angular position i=0 that can correspond to any relative angle between the rigid endoscope and the camera-head. With the lens scope at the reference angular position, the user starts by acquiring K≥1 calibration images. Intrinsic camera calibration as described in §§ [0045]-[0049] (Module A) is then performed by extracting 2D-3D correspondences $x_i^k$, $X_i^k$ for each image, and retrieving the calibration object poses $R_i^k$, $t_i^k$, as well as a set of intrinsic parameters $K(f_i, O_i)$ and distortion $\xi_i$. The circular boundary with center $C_i$, radius $r_i$ and notch $P_i$ are also detected by following the method described in §§ [0050]-[0057] (Module B). This data is stored in memory, giving the user the option of changing the angular position by rotating the lens scope with respect to camera-head, and repeating the processes of image acquisition, intrinsic calibration and boundary/notch detection. This is performed for a total of N>1 distinct angular positions i, with i=0, 1, . . . N−1 and i=0 being the reference angular position for which the final calibration is obtained after a global optimization step that fuses the estimates at each position i and minimizes the re-projection error for all calibration images in simultaneous (FIG. 8).

The off-line calibration method of FIG. 7 can be carried using frames acquired at a single angular position, in which case N=1 and the position is the reference position i=0, or at multiple angular positions, in which case N>1. For each different position it can be acquired either a single calibration frame (K=1), or multiple calibration frames (K>1).

The case N=1 and K=1 is the one that requires minimum user effort, being particularly well suited for fast calibration in the OR where the surgeon just has to acquire a single image of the checkerboard pattern after assembling the endoscope in the camera head. The accuracy in the estimation of the calibration parameters tends to improve for an increasing number K of frames.

The use of information from two or more angular positions (N>1) makes it possible to estimate the rotation center Q in conjunction with f, $\xi$ and $O_0$, independently of the number K of frames acquired at each position. This can be accomplished by following the approach depicted in FIG. 4 and disclosed in §§ [0058]-[0064]. For N>1, the calibrations obtained at different angular positions are fused in a large-scale optimization step that enforces the rotation model, as illustrated in FIG. 8 for N=3. It can be observed that for any two angular positions, the principal point O and notch P rotate by the same amount $\delta$ around the rotation center Q. The optimization scheme serves to estimate the distortion and the calibration parameters at the reference position, while minimizing the re-projection error in all acquired calibration images and enforcing this model for the scope rotation for all sampled angular positions simultaneously. The expression present in FIG. 8 provides the mathematical formulation for this optimization scheme for the case of N=3 angular positions, being straightforward to extend to a generic value N. Function r computes the squared reprojection error by projecting points $X_i^k$ onto the image plane, yielding $\hat{x}_i^k$, and outputting the squared distances $d(\hat{x}_i^k, x_i^k)^2$, with d being the Euclidean distance between points $\hat{x}_i^k$ and $x_i^k$. $K_i$ is the number of calibration images acquired with the scope in the angular position i. As evinced by the mathematical expression, the proposed optimization scheme finds the values for the distortion $\xi$, rotation center Q, intrinsic parameters f and $O_0$, as well as the calibration object poses $R_i^k$, $t_i^k$, that minimize the sum of the reprojection error computed for all frames k and angular positions i.

2.5 Online Update of the Calibration Parameters

During operation, every time a new frame j is acquired, an on-the-fly procedure must detect and measure the angular displacement with respect to the reference position and update the calibration and camera model accordingly. FIG. 9 gives a schematic description of this procedure. Frame j is processed for the detection of the circular boundary center $C_j$ and the notch $P_j$, which can be accomplished by following the steps disclosed in FIG. 3 and §§ [0050]-[0057]. Afterwards, the estimation of the angular displacement $\delta_j$ is performed as disclosed in §§ [0058]-[0064] for which the rotation center Q must be known.

There are two possible modes of operation for retrieving Q: in mode 1 the rotation center is known in advance from the offline calibration step that used frames acquired in N>1 angular positions as disclosed in §§ [0065]-[0069]; in mode 2, the rotation center is not known 'a priori' but estimated on-the-fly from successive frames for which the notch P and/or center of circular boundary C are determined such that the methods disclosed in §§ [0058]-[0064] and FIG. 4 can be employed. As illustrated in FIG. 9, the current notch $P_j$ and center $C_j$ are used in conjunction with the ones detected on the previous frame j−1, which is accessed through a delay operation, $P_{j-1}$ and center $C_{j-1}$, to estimate the rotation center Q. As a final step, the calibration parameters are updated by applying a plane rotation to the principal point $O_0$ corresponding to the reference position, i.e., by computing the updated principal point as $O_j=R(\delta_j,Q)O_0$

3. Off-Site Lens Calibration to Avoid Explicit Calibration Steps in the OR

It has been disclosed a method to determine the calibration of an endoscopic camera at all times that comprises two steps or stages: an offline step that aims to estimate the focal length f, the distortion and the principal point O for an arbitrary reference angular position, and an online step that determines at every frame time instant the angular displacement with respect to the reference and updates the position of the principal point to provide the calibration for the current frame. Since the lens of the endoscopic camera is exchangeable, both offline and online steps are carried on-site in the OR after the surgeon assembles the endoscope in the camera-head. While the online step is meant to run on-the-fly, in parallel with image acquisition in a seamless manner to user, the offline step requires explicit user intervention to acquire one or more calibration frames, which is undesirable.

In order to minimize disruption to the existing surgical workflow, U.S. Pat. No. 9,438,897 B2 describes a method that is the particular situation of N=1 and K=1 of the offline step disclosed in §§ [0065]-[0069] and FIG. 7. The effort of the surgeon is minimized by requiring the acquisition of a single frame at the reference position, and the rotation center Q is determined in the online step as in mode 2 of FIG. 9. Nevertheless, the method still requires surgeon intervention in the OR, which is still time-consuming and a disruption to the workflow, and it requires the use of a sterile calibration object (in this case a checkerboard pattern) which is not always easy to produce and adds cost.

This patent overcomes these problems by disclosing a method for calibrating the endoscopic lens alone, which can be performed off-site (e.g. at manufacture) with the help of a camera or other means, and that provides a set of parameters that fully characterize the rigid endoscope leading to a lens descriptor $\dot{\Phi}$ that can be used for different purposes. One of these purposes is to accomplish calibration of any endoscopic camera system that is equipped with the lens, in which case the descriptor $\dot{\Phi}$ is loaded in the Camera Control Unit (CCU), to be used as input in an online method that runs on-the-fly, and that outputs the complete calibration of the camera-head+lens arrangement at every frame time instant.

Since the lens calibration can be carried off-site, namely in factory at the time of manufacture, and the online calibration runs on-the-fly in a seamless manner to the user, there is no action to be carried in the OR by the surgeon, which means that endoscopic camera calibration is accomplished at all times with no change or disruption of the established routines. Moreover, and differently from what is possible with the method disclosed in U.S. Pat. No. 9,438,897 B2, calibration is accomplished even in situations of variable zoom and/or translation of the lens with respect to camera-head.

The method of off-site, offline calibration of the rigid endoscope to generate the descriptor $\dot{\Phi}$ is disclosed in §§ [0079]-[0083], while the online method to accomplish calibration of endoscopic camera comprising camera-head and optics is described in §§ [0084]-[0085].

3.1 Off-Site, Offline Lens Calibration

The rigid endoscope is assembled in an arbitrary camera-head, henceforth referred to as the Characterization Camera, and the offline calibration method of FIG. 7, §§ [0065]-[0069] is employed, which requires acquiring K calibration images at N distinct angular positions. This enables to calibrate at the reference angular position i=0, which includes knowing the intrinsic parameters K(f, O), the distortion ξ, the notch P, the circular boundary Ω with center C and radius r, and, if N>1, the rotation center Q.

The calibration result refers to the compound arrangement of camera-head with rigid endoscope, with the measurements depending on the particular camera-head in use, as well as on the manner the lens is mounted in the camera-head. Since the objective is to characterize the endoscope alone, the influence of the camera-head must be removed such that the final descriptor only depends on the lens and is invariant to the camera and/or equipment employed to generate it.

The method herein disclosed accomplishes this objective by building in two key observations: (i) the camera-head usually follows an orthographic (or nearly orthographic) projection model, which means that it only contributes to the imaging process with magnification and conversion of metric units to pixels; and (ii) the images of the Field-Stop-Mask (FSM) always relate by a similarity transformation, which means the FSM can be used as a reference to encode information about the lens that is invariant to rigid motion and scaling.

Figure 10:
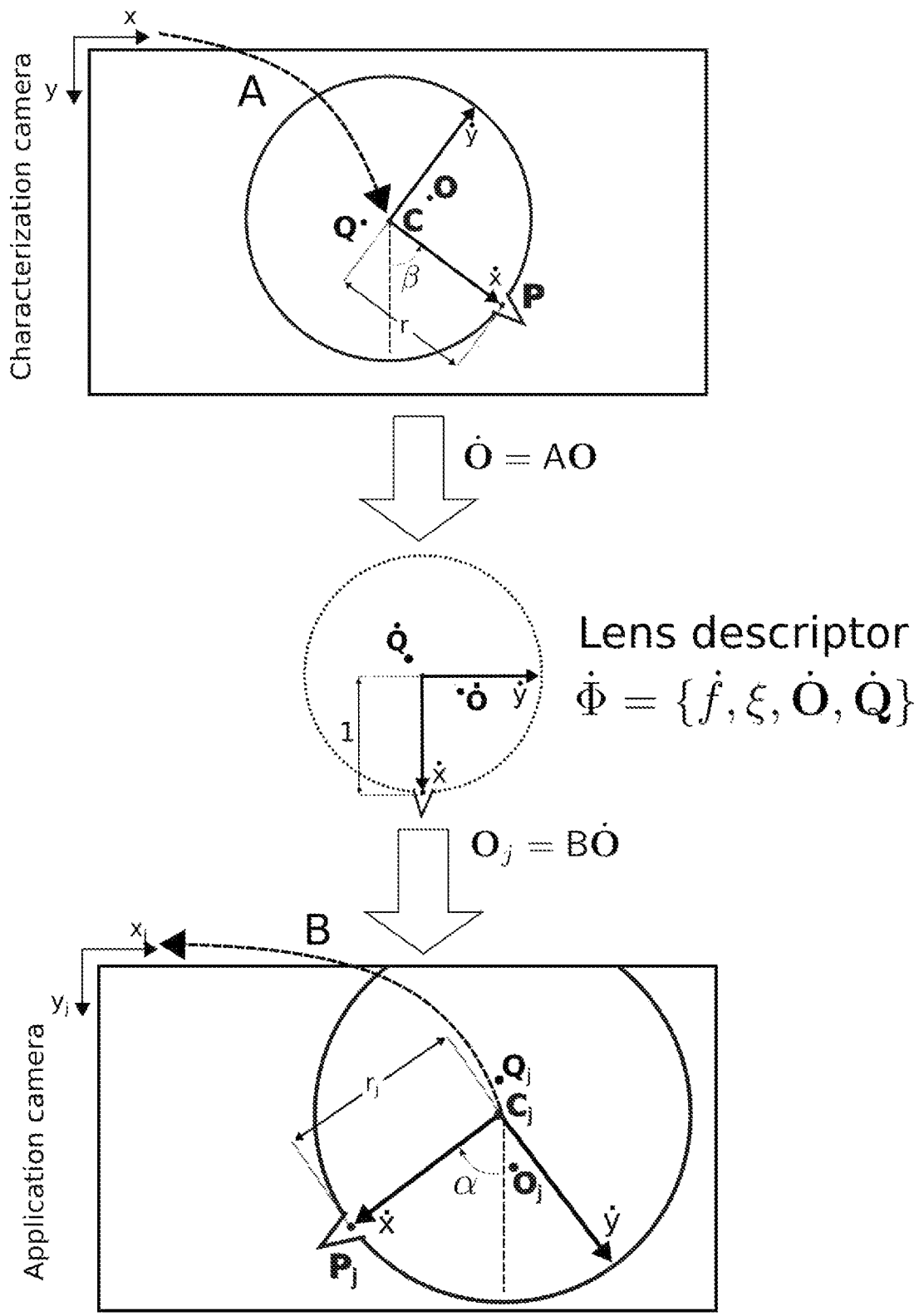
FIG. 10 illustrates the process of decoupling the parameters of a lens included in a camera system, denoted as characterization camera, from the contribution of the camera head, yielding a lens descriptor $\dot{\Phi}=\{\dot{f}, \dot{\xi}, \dot{O}, \dot{Q}\}$, as well as the estimation of the calibration parameters of a new camera system (the application camera), equipped with the same lens, by making use of its descriptor $\dot{\Phi}$. From a frame acquired with the characterization camera, an auxiliary reference frame attached to the boundary, that is obtained by transforming the reference frame of the image by a similarity transformation A, is considered. By representing the calibration parameters in boundary coordinates, the lens descriptor $\dot{\Phi}$ is obtained. In order to obtain the calibration of the application camera, that is equipped with the same endoscopic lens, a similarity transformation B is employed for converting the entries of the lens descriptor $\dot{\Phi}$, that are represented in boundary coordinates, into image coordinates.

Let the calibration result after applying the offline method of FIG. 7 comprise the focal length f, the distortion ξ, the principal point O, the notch P, and the circular boundary Ω with center C and radius r. The lens descriptor is $\dot{\Phi}=\{\dot{f}, \dot{\xi}, \dot{O}\}$, with $\dot{f}=f/r$, where the division by r works as a normalization to account for the magnification introduced by the camera-head, ξ is as measured in the offline calibration step because it is a characteristic intrinsic to the optics that is not influenced by the camera-head, and $\dot{O}$ is the principal point referenced in a system of coordinates attached to the circular boundary (the lens coordinate system), with center in C and x axis aligned with the segment joining the center C and the notch P after being scaled by r (FIG. 10). For this particular choice of lens reference frame, the change of coordinates between image and lens is performed by a similarity transformation A such that $\dot{O}=AO$ with A=

$$\begin{bmatrix} \cos\beta & -\sin\beta & -C_x\cos\beta + C_y\sin\beta \\ \sin\beta & \cos\beta & -C_x\sin\beta + C_y\cos\beta \\ 0 & 0 & r \end{bmatrix},$$

and β is angle between the x axes of the image and boundary reference frames. If the rotation center Q is known, then it can also be represented in lens coordinates by making $\dot{Q}=AQ$ and stacked to the descriptor, that becomes $\dot{\Phi}=\{\dot{f}, \dot{\xi}, \dot{O}, \dot{Q}\}$. These particular choices of image and lens reference frames are arbitrary, and other reference frames, related by rigid transformations with the chosen ones, could have been considered without compromising the disclosed methods.

3.2 Online Camera Calibration Using the Lens Descriptor

When the lens with descriptor $\dot{\Phi}$ is mounted on an arbitrary camera head, henceforth referred to as application camera, it is possible to automatically obtain the calibration of the full arrangement camera+lens by proceeding as follows: for each frame j, apply the method of FIG. 3 to detect the position of both the notch $P_j$ and the circular boundary with center q and radius $r_j$; find the location of the lens reference frame in the image and determine the similarity transformation B that maps lens coordinates into current image coordinates, with B=

$$\begin{bmatrix} r_j\cos\alpha & r_j\sin\alpha & C_{jx} \\ -r_j\sin\alpha & r_j\cos\alpha & C_{jy} \\ 0 & 0 & 1 \end{bmatrix},$$

where $\alpha$ is the angle between the x axes of the two reference frames; finally, the calibration of the endoscopic camera for the current angular position can be determined by decoding the different descriptor entries, in which case the focal length becomes $f_j=r_j\hat{f}$, the principal point is now $O_j=B\dot{O}$ and the distortion $\xi$ is the same because it is inherent to the optics. If the descriptor also comprises the rotation center, then its position in frame j can be determined in a similar manner by making $Q_j=B\dot{Q}$.

3.3 Relevant Considerations

Off-site offline lens calibration using a single image: One important consideration is that the calibration approach disclosed in this patent does not require the knowledge of the rotation center Q for determining the calibration of the endoscopic camera at every frame time instant. Thus, if time and effort of the off-site calibration procedure is a concern, the lens descriptor can be generated by acquiring a single calibration image in which case the offline method of FIG. 7, §§ [0065]-[0069] is run with K=1 and N=1. In this case the descriptor will not include the entry Q.

Accommodation of relative rotation (calibration by detection or by tracking): Since a rotation of the endoscope with respect to the camera-head $\delta_j$ causes a similar rotation to the lens reference frame in the image, the update of the calibration at every frame j can be performed implicitly without having to compute an angular displacement $\delta_j$ and explicitly rotate the principal point around the center Q. In this case, the disclosed approach based on the lens descriptor can be used alone, with $\dot{\Phi}$ being decoded at every frame time instant by the online method of §§ [0084]-[0085] (calibration by detection). An alternative is to employ the method of FIG. 9, §§ [0070]-[0072], in which case the lens descriptor is used to obtain the calibration at an arbitrary reference position, and this calibration is then updated by determining angular displacements $\delta_j$ and rotating the principal point (calibration by tracking).

Adaptation to optical zoom and/or translation of the lens scope along the plane orthogonal to the mechanical axis: In the disclosure, the focal length $f_j$ is determined at each frame time instant by scaling the normalized focal length $\hat{f}$ by the magnification introduced by the application camera, which is inferred from the radius $r_j$ of the circular boundary. If the magnification is constant, then $f_j$ is also constant across successive frames j. However, if the application camera has optical zoom that varies, then f will vary accordingly. Thus, and unlike the method described in U.S. Pat. No. 9,438,897 B2, the method herein disclosed can cope with changes in zoom, as well as with translations of the lens scope along the plane orthogonal to the mechanical axis. The adaptation to the former stems from the fact that changes in zoom lead to changes in the radius of the boundary $r_j$ that is used to decode the relevant entries in the lens descriptor, namely $f_j$, $O_j$ and $Q_j$, providing the desired adaptation. The adjustment to the latter arises from the fact that the circular boundary, to which the lens coordinate system is attached, translates with the lens, and the image coordinates of the decoded $O_j$ and $Q_j$ translate accordingly.

Figure 11:
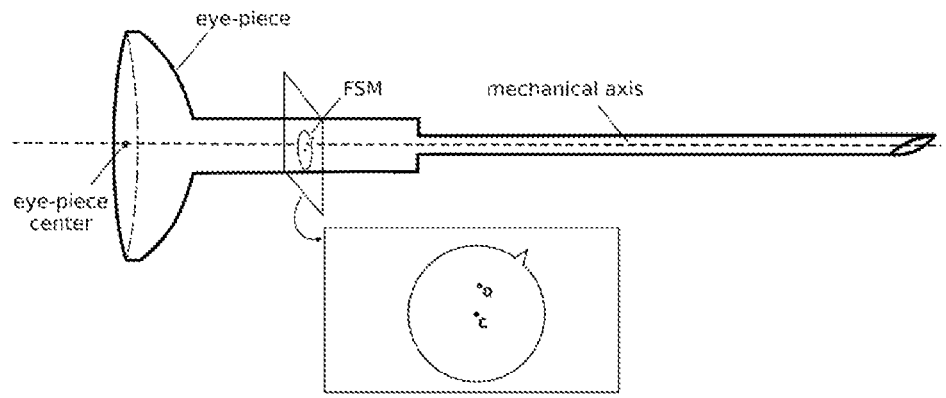
FIG. 11 is an embodiment of the components of an endoscope, illustrating how the rotation center and the center of the FSM are related. This allows to better understand the physical meaning of the lens descriptor disclosed in this patent.

Alternative means to generate the lens descriptor: The descriptor $\dot{\Phi}=\{\dot{f}, \dot{\xi}, \dot{O}, \dot{Q}\}$ characterizes the lens through parameters or features that have a clear physical meaning. For example, the mechanical axis of the endoscope, that is in general defined by the symmetry axis of the eye-piece in the proximal end of the lens, should go through the center of the circle defined by the FSM. If this condition holds, then the center C and the rotation center Q are coincident and $\dot{Q}=[0,0,1]^T$. In general, the condition is not verified, as illustrated in FIG. 11, because of mechanical tolerances in the manufacturing process, in which case the non-zero $\dot{Q}$ accounts for the misalignment between eye-piece and FSM. Since it is a mechanical misalignment, it can be potentially measured by other means than the ones disclosed in §§ [0079]-[0083] using camera calibration and image processing to generate $\dot{\Phi}$. Such alternative means include using a caliper, micrometer, protractor, gauges, robotic measurement apparatuses or any combination of thereof, to physically measure the distance between axis and center of the FSM.

Transmission of the lens descriptor to Application Camera: In the disclosed embodiment the lens descriptor is generated off-site with the help of a Characterization Camera, and must be then communicated to the CCU or computer platform connected to the Application Camera that will execute the online method of §§ [0084]-[0085] (FIG. 10). This transmission or communication can be accomplished through a multitude of methods that include, but are not limited to, manual insertion of the calibration parameters onto the CCU by means of a keyboard or other input interface, network connection and download from a remote server, retrieval from a database of lens descriptors, reading from a USB flash drive or any other storage medium, visual reading and decoding of a QR code, visual reading and decoding of information engraved in the FSM such as digits or binary codes as disclosed in PCT/US2018/048322.

Descriptor for a batch of lenses: The descriptor $\dot{\Phi}$ can either characterize a specific lens or be representative of a batch of lenses with similar characteristics. In this last case, the descriptor can be generated by either using as input to the off-line calibration method of FIG. 7 calibration frames acquired with different lenses in the batch, in which case a single descriptor is enforced in the final global optimization step or, in alternative, by generating a descriptor for each lens in the batch and averaging their entries to obtain a single representation. The characterization of a batch of lenses by a single average descriptor can avoid the need of loading a specific descriptor for each lens used in a certain Application Camera, or be used for the purpose of quality control in production, in which case the variance of the parameters in the descriptor is a measurement of the repeatability of the manufacturing processes.

4. Detection of Anomalies in the Endoscopic Camera

While the calibration approach presented in §§ [0041]-[0072] always provides a correct calibration of the endoscopic camera, as it is assembled and explicitly calibrated in the OR, the calibration method disclosed in this patent (§§ [0073]-[0092]) relies on prior assumptions such as the correct retrieval of stored calibration information and the proper assembly of the lens in the camera head. In case these assumptions are not satisfied, the camera+lens arrangement will not be accurately calibrated and malfunctions can occur in systems that use the calibration information for performing distortion correction, virtual views rendering, enhanced visualization, surgical navigation, etc.

This patent discloses a method that makes use of the lens descriptor $\dot{\Phi}$ for detecting anomalies in the endoscopic camera calibration caused by a mismatch between the loaded calibration information and the lens in use and/or an incorrect assembly of the lens in the camera head or a defect of any of these components.

Figure 12:
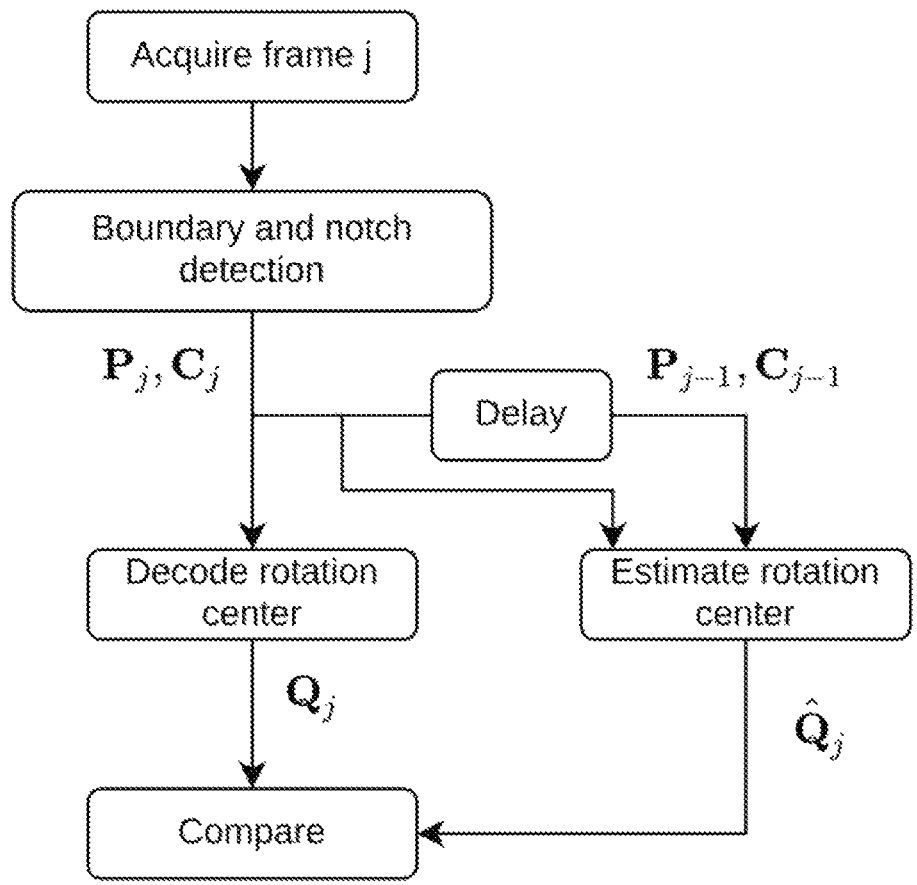
FIG. 12 shows the sequence of steps of the anomaly detection procedure. For each acquired frame j, detection of the boundary and notch is performed both for obtaining the updated calibration from the lens descriptor and for estimating the rotation center using the previously detected boundary and notch. This yields two different estimates for the rotation center ($Q_j$ and $\overline{Q}_j$), that are compared and allow the detection of an anomaly.

FIG. 12 provides a schematic description of this method for anomaly detection. For each acquired frame j, detection of the boundary and notch is performed both for obtaining the updated calibration from the loaded lens descriptor, as described in §§ [0084]-[0085], and for estimating the rotation center, as described in §§ [0058]-[0064]. This yields two different estimates for the rotation center ($Q_j$ and $\widehat{Q}_j$ in FIG. 12), that can be compared to detect an anomaly. The intuition behind this approach is the following: Two lenses do not rotate in the exact same manner because of mechanical tolerances in building the optics. Thus, the way each lens rotates with respect to any camera-head can work as a signature to distinguish it from the others. In addition, if the lens is incorrectly assembled or damaged, because of a defect/damage in the eye piece connector, a defect/damage to the lens itself or any other aspect that leads to a defective fit between the camera and lens, it will also rotate differently from how it rotates when properly assembled.

This change in the lens motion model can be used to detect the existence of an anomaly, as well as to quantify how serious the anomaly is, and warn the user to verify the assemblage and/or replace the lens.

This method only provides information on the existence of an anomaly, and does not specify which type of anomaly is occurring, which would allow the system to provide the user specific instructions for fixing the anomaly. To accomplish this, the approach for anomaly detection schematized in FIG. 12 can be complemented with another method for identifying the cause of anomaly. Since an incorrect assembly of the lens in the camera-head causes a modification to the projection of the FSM in the image plane, a feature that quantifies the difference between the boundaries detected at calibration and operation time can be used to distinguish between an anomaly caused by calibration-optics mismatch or a deficient assembly.

In particular, if the FSM is projected in the image plane onto a circle when the lens is properly assembled in the camera-head, this circle tends to evolve into an ellipse when the optics is not correctly assembled. Thus, in this case, the eccentricity of the boundary detected during operation can be measured to verify if the assemblage is correct, and it is not required to know the specific shape of the boundary detected during calibration of the lens.

This approach is valid if the FSM has a shape that can be represented parametrically, such as an ellipse or any other geometric shape. In addition, template matching or machine learning techniques can be used to compare the boundary detected during operation with the known shape.

Summarizing, there exist two important features that can be used for detecting and identifying anomalies. The first one is the difference between the rotation center estimates obtained at calibration time and during operation, $Q_j$ and $\widehat{Q}_j$, respectively. The second consists in the difference between the boundary contours detected at calibration time and during operation. While the first allows the detection of an anomaly, whether it is a mismatch between the loaded calibration and the camera+lens arrangement in use, an incorrect assembly of the lens in the camera head or a defect of any of these components, the second provides information on the type of anomaly since it only occurs when there is a deficient assemblage.

Thus, the disclosed method for detection and identification of anomalies that makes use of these two distinct features can be implemented using a cascaded classifier that starts by using the first feature for the anomaly detection stage and then discriminates between a calibration mismatch and an incorrect camera+lens assembly by making use of the second feature. In alternative to the cascaded classifier, other methods such as different types of classifiers, machine learning, statistical approaches, data mining can be employed. In addition, depending on the desired application, these features can be used individually, in which case the first feature would allow the detection of an anomaly, without identification of the type of anomaly, and the second feature would solely serve to detect incorrect assemblages.

Figure 13:
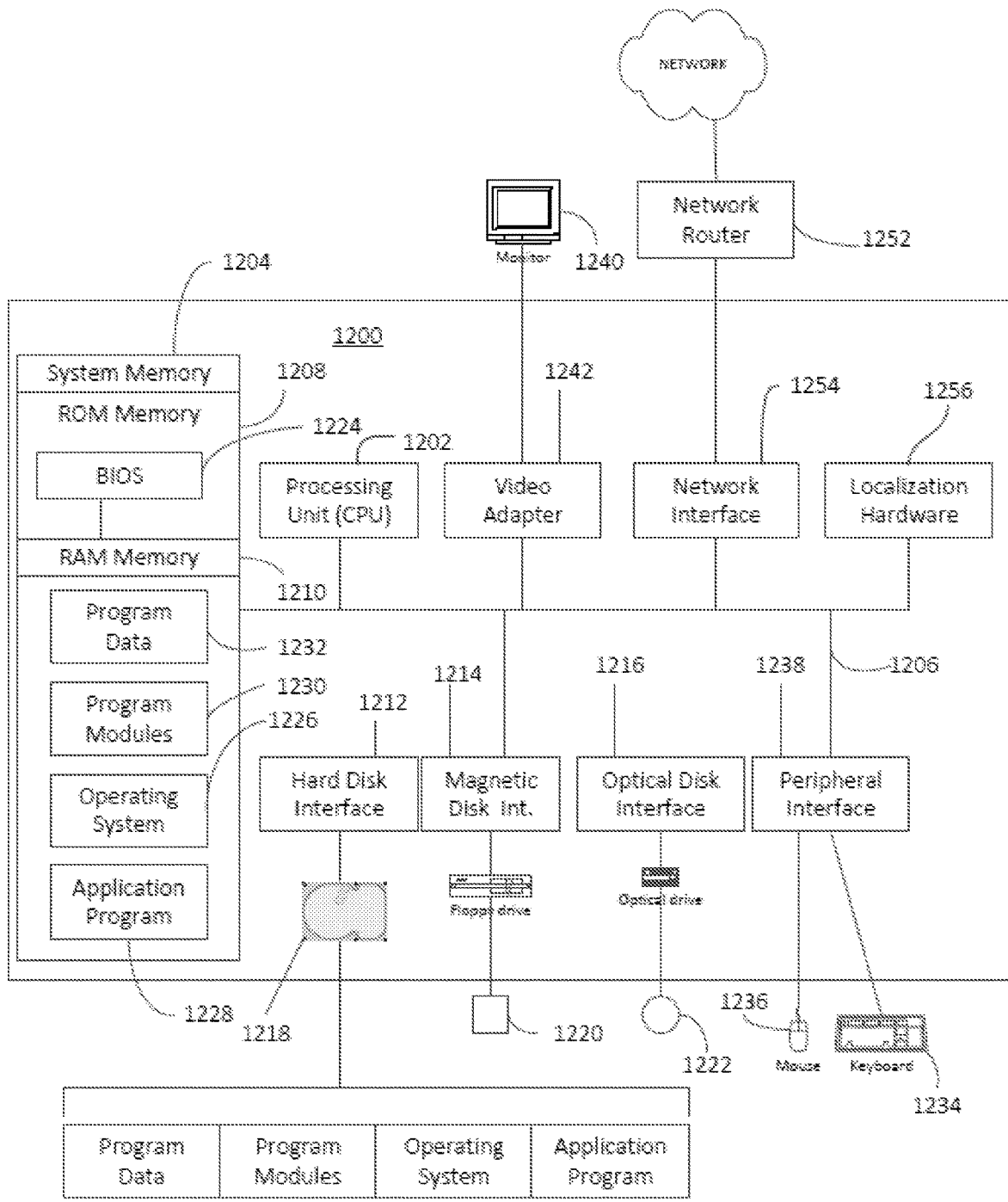
FIG. 13 is a diagrammatic view of an example computing system that includes a general purpose computing system environment.

FIG. 13 is a diagrammatic view of an illustrative computing system that includes a general purpose computing system environment 1200, such as a desktop computer, laptop, smartphone, tablet, or any other such device having the ability to execute instructions, such as those stored within a non-transient, computer-readable medium. Furthermore, while described and illustrated in the context of a single computing system 1200, those skilled in the art will also appreciate that the various tasks described hereinafter may be practiced in a distributed environment having multiple computing systems 1200 linked via a local or wide-area network in which the executable instructions may be associated with and/or executed by one or more of multiple computing systems 1200. Computing system environment 1200, or portions thereof, may find use for the processing, methods, and computing steps of this disclosure.

In its most basic configuration, computing system environment 1200 typically includes at least one processing unit 1202 and at least one memory 1204, which may be linked via a bus 1206. Depending on the exact configuration and type of computing system environment, memory 1204 may be volatile (such as RAM 1210), non-volatile (such as ROM 1208, flash memory, etc.) or some combination of the two. Computing system environment 1200 may have additional features and/or functionality. For example, computing system environment 1200 may also include additional storage (removable and/or non-removable) including, but not limited to, magnetic or optical disks, tape drives and/or flash drives. Such additional memory devices may be made accessible to the computing system environment 1200 by means of, for example, a hard disk drive interface 1212, a magnetic disk drive interface 1214, and/or an optical disk drive interface 1216. As will be understood, these devices, which would be linked to the system bus 1206, respectively, allow for reading from and writing to a hard disk 1218, reading from or writing to a removable magnetic disk 1220, and/or for reading from or writing to a removable optical disk 1222, such as a CD/DVD ROM or other optical media. The drive interfaces and their associated computer-readable media allow for the nonvolatile storage of computer readable instructions, data structures, program modules and other data for the computing system environment 1200. Those skilled in the art will further appreciate that other types of computer readable media that can store data may be used for this same purpose. Examples of such media devices include, but are not limited to, magnetic cassettes, flash memory cards, digital videodisks, Bernoulli cartridges, random access memories, nano-drives, memory sticks, other read/write and/or read-only memories and/or any other method or technology for storage of information such as computer readable instructions, data structures, program modules or other data. Any such computer storage media may be part of computing system environment 1200.

A number of program modules may be stored in one or more of the memory/media devices. For example, a basic input/output system (BIOS) 1224, containing the basic routines that help to transfer information between elements within the computing system environment 1200, such as during start-up, may be stored in ROM 1208. Similarly, RAM 1210, hard drive 1218, and/or peripheral memory devices may be used to store computer executable instructions comprising an operating system 1226, one or more applications programs 1228 (such as an application that performs the methods and processes of this disclosure), other program modules 1230, and/or program data 1232. Still further, computer-executable instructions may be downloaded to the computing environment 1200 as needed, for example, via a network connection.

An end-user, e.g., a customer, retail associate, and the like, may enter commands and information into the computing system environment 1200 through input devices such as a keyboard 1234 and/or a pointing device 1236. While not illustrated, other input devices may include a microphone, a joystick, a game pad, a scanner, etc. These and other input devices would typically be connected to the processing unit 1202 by means of a peripheral interface 1238 which, in turn, would be coupled to bus 1206. Input devices may be directly or indirectly connected to processor 1202 via interfaces such as, for example, a parallel port, game port, firewire, or a universal serial bus (USB). To view information from the computing system environment 1200, a monitor 1240 or other type of display device may also be connected to bus 1206 via an interface, such as via video adapter 1242. In addition to the monitor 1240, the computing system environment 1200 may also include other peripheral output devices, not shown, such as speakers and printers.

The computing system environment 1200 may also utilize logical connections to one or more computing system environments. Communications between the computing system environment 1200 and the remote computing system environment may be exchanged via a further processing device, such as a network router 1252, that is responsible for network routing. Communications with the network router 1252 may be performed via a network interface component 1254. Thus, within such a networked environment, e.g., the Internet, World Wide Web, LAN, or other like type of wired or wireless network, it will be appreciated that program modules depicted relative to the computing system environment 1200, or portions thereof, may be stored in the memory storage device(s) of the computing system environment 1200.

The computing system environment 1200 may also include localization hardware 1256 for determining a location of the computing system environment 1200. In embodiments, the localization hardware 1256 may include, for example only, a GPS antenna, an RFID chip or reader, a Wi-Fi antenna, or other computing hardware that may be used to capture or transmit signals that may be used to determine the location of the computing system environment 1200.

In a first aspect of this disclosure, a method for calibrating an endoscopic camera is provided. The endoscopic camera results from combining a rigid endoscope with a camera, wherein the rigid endoscope or lens scope has a Field Stop Mask (FSM) that renders an image boundary with center C and a notch P, and can rotate with respect to the camera-head by an angle $\delta$ around a mechanical axis that intersects the image plane in point Q, in which case C, P and the principal point O undergo a 2D rotation of the same angle $\delta$ around Q, and wherein calibration consists in determining the focal length f, distortion $\xi$, rotation center Q and principal point $O_0$ for a chosen angular position of the lens scope with respect to the camera-head, henceforth referred to as the reference angular position i=0. The method comprises: acquiring one or more calibration images of a calibration object with the endoscopic camera at angular position i without rotating the lens with respect to the camera head; determining a first estimate of the calibration parameters f, $\xi$ and $O_i$ of the endoscopic camera, as well as the 3D pose (rotation and translation) of the calibration object with respect to the camera for each calibration image; detecting a boundary with center $C_i$ and notch $P_i$ on the calibration images using an image processing method; rotating the lens scope with respect to the camera-head to a new angular position i and repeating the previous steps, with i being incremented to take successive values i=0, 1, . . . , N−1 where N≥1 is the number of different angular positions used for the calibration; determining a first estimate for the rotation center Q and for the angular displacements $\delta_i$ between the reference position i=0 and the successive calibration positions i=1, . . . N−1; and refining the calibration parameters f, $\xi$, Q, and $O_0$ through a final optimization step that enforces the model of the principal point, boundary center, and notch undergoing a rotation by an angle $\delta'$ around the center Q for successive calibration positions i=0, . . . N−1.

In an embodiment of the first aspect, the calibration object is either a 2D plane with a checkerboard pattern or any other known pattern, a known 3D object, or is non-existent, with the calibration input being a set of point correspondences across images, in which case the first estimate of the calibration parameters are respectively obtained by a camera calibration algorithm from planes, a camera calibration algorithm from objects, or a suitable auto-calibration technique.

In an embodiment of the first aspect, the final optimization step is performed using an iterative non-linear minimization of a reprojection error, photogeometric error, or any other suitable optimization approach.

In an embodiment of the first aspect, the first estimate of the calibration parameters is determined from any calibration method in the literature.

In an embodiment of the first aspect, the first estimate of the calibration parameters includes any distortion model known in the literature such as Brown's polynomial model, the rational model, the fish-eye model, or the division model with one or more parameters, in which case is a scalar or a vector, respectively.

In an embodiment of the first aspect, the rotation center Q is known in advance, in which case the calibration can be accomplished from images acquired in one or more angular positions (N>=1), is determined from the image position of boundary centers $C_i$ and notches $P_i$, in which case the calibration is accomplished from images acquired in two or more angular positions (N>=2), or is determined solely from image position of boundary centers $C_i$ or notches $P_i$, in which case the calibration is accomplished from images acquired in three or more angular positions (N>=3).

In a second aspect of the present disclosure, a method for updating, at every frame time instant, the calibration parameters of an endoscopic camera is provided. The endoscopic camera results from combining a rigid endoscope with a camera comprising a camera-head and a Camera Control Unit (CCU), wherein the rigid endoscope or lens scope has a Field Stop Mask (FSM) that renders an image boundary with center C and a notch P, and can rotate with respect to the camera-head by an angle $\delta$ around a mechanical axis that intersects the image plane in point Q, in which case C, P and the principal point O undergo a 2D rotation of the same angle δ around Q, and wherein the calibration parameters focal length f, distortion ξ, rotation center Q and principal point $O_0$, as well as a boundary with center $C_0$ and a notch $P_0$, for a reference angular position i=0 of the lens scope with respect to the camera-head are known. The method comprises: acquiring a new frame j by the endoscopic camera and detecting a boundary center $C_j$ and a notch $P_j$; estimating an angular displacement δ of the endoscopic lens with respect to the camera-head according to notch $P_0$, notch $P_j$ and Q; and estimating an updated principal point $O_j$ of the endoscopic camera by performing a 2D rotation of the principal point $O_0$ around Q by an angle δ.

In an embodiment of the second aspect, the calibration parameters focal length f, distortion ξ, rotation center Q and principal point $O_0$, as well as a boundary with center $C_0$ and a notch $P_0$, at the reference angular position i=0 are obtained by calibrating the endoscopic camera with the lens scope at the reference position or by retrieval from the CCU.

In an embodiment of the second aspect, the rotation center Q is determined using two or more boundary centers $C_j$ and/or notches $P_j$.

In an embodiment of the second aspect, the angular displacement of the endoscopic lens is estimated by mechanical means and/or by making use of optical tracking, in which case the boundary centers $C_0$ and $C_j$ and the notches $P_0$ and $P_j$ do not have to be known.

In an embodiment of the second aspect, the method further comprises employing a technique for filtering the estimation of the rotation center Q and the angular displacement δ including, but not limited to, any recursive or temporal filter known in the literature such as a Kalman filter or an Extended Kalman filter.

In a third aspect of the present disclosure, a method for characterizing a rigid endoscope with a Field Stop Mask (FSM) that induces an image boundary with center C and a notch P by obtaining a descriptor $\dot{\Phi}$ comprising a normalized focal length $\dot{f}$, a distortion ξ, a normalized principal point $\dot{O}$ and a normalized rotation center $\dot{Q}$ is provided, the method comprising: combining the rigid endoscope with a camera to obtain an endoscopic camera, referred to as characterization camera; estimating the calibration parameters (focal length f, distortion ξ, principal point $O_0$ and rotation center Q) of the characterization camera at a reference position; detecting a boundary with center $C_0$ and a notch $P_0$ at the reference position; and determining the normalized focal length $\dot{f}$, normalized principal point $\dot{O}$ and normalized rotation center $\dot{Q}$ according to center $C_0$, notch $P_0$, focal length f, principal point $O_0$ and rotation center Q.

In an embodiment of the third aspect, the normalized focal length $\dot{f}$ is computed from $\dot{f}=f/r$, with r being the distance between center $C_0=[C_x, C_y, 1]^T$ and notch $P_0$, and the normalized principal point $\dot{O}$ and rotation center $\dot{Q}$ are obtained by computing $\dot{O}=AO$ and $\dot{Q}=AQ$, respectively, with A=

$$A = \begin{bmatrix} \cos\beta & -\sin\beta & -C_x\cos\beta + C_y\sin\beta \\ \sin\beta & \cos\beta & -C_x\sin\beta + C_y\cos\beta \\ 0 & 0 & r \end{bmatrix}$$

and β being the angle between line $\overline{CP}$ and the down direction.

In a fourth aspect of the present disclosure, a method for calibrating an endoscopic camera is provided. The endoscopic camera results from combining a rigid endoscope with a camera comprising a camera-head and a Camera Control Unit (CCU), wherein the rigid endoscope has a descriptor $\dot{\Phi}$ comprising a normalized focal length $\dot{f}$, a distortion ξ, a normalized principal point $\dot{O}$ and a normalized rotation center $\dot{Q}$ and has a Field Stop Mask (FSM) that renders an image boundary with center C and a notch P, and wherein calibration consists in determining the focal length f, distortion ξ, rotation center Q and principal point O for a particular angular position of the lens scope with respect to the camera-head. The method comprises: acquiring frame i by the endoscopic camera, detecting a boundary center $C_i=[C_x, C_y, 1]^T$ and a notch $P_i$, and determining a radius $r=\|C_iP_i\|-$; and estimating the calibration parameters of the endoscopic camera focal length f, rotation center Q and principal point O according to center center $C_i$, notch $P_i$, the normalized focal length $\dot{f}$, the normalized principal point $\dot{O}$ and the normalized rotation center $\dot{Q}$.

In an embodiment of the fourth aspect, the focal length f, the principal point O and the rotation center Q are computed by $f=r\dot{f}$, $O=B\dot{O}$ and $Q=B\dot{Q}$, respectively, with B=

$$\begin{bmatrix} r\cos\alpha & r\sin\alpha & C_x \\ -r\sin\alpha & r\cos\alpha & C_y \\ 0 & 0 & 1 \end{bmatrix}$$

and α being the angle between line $\|\overline{C_iP_i}\|$ and the down direction.

In an embodiment of the fourth aspect, the endoscopic lens descriptor $\dot{\Phi}$ is obtained by using a camera, by measuring the endoscopic lens using a caliper, a micrometer, a protractor, gauges, robotic measurement apparatuses or any combination of thereof or by using a CAD model of the endoscopic lens.

In an embodiment of the fourth aspect, the endoscopic lens descriptor $\dot{\Phi}$ is obtained by loading information into the CCU from a database or using QR codes, USB flash drives, manual insertion, engravings in the FSM, RFID tags, an internet connection, etc.

In an embodiment of the fourth aspect, frame i comprises two or more frames, wherein the rotation center Q is determined using two or more boundary centers $C_i$ and/or notches $P_i$.

In an embodiment of the fourth aspect, the endoscopic camera can have an arbitrary angular position of the lens scope with respect to the camera-head and an arbitrary amount of zoom.

In a fifth aspect of the present disclosure, a method for detecting an anomaly caused by defects or incorrect assembly of a rigid endoscope in a camera-head or by a mismatch between a considered calibration and an endoscopic lens in use in an endoscopic camera that results from combining the rigid endoscope with a camera comprising the camera-head and a Camera Control Unit (CCU), wherein the rigid endoscope has a descriptor $\dot{\Phi}$ comprising a normalized rotation center $\dot{Q}$ and has a Field Stop Mask (FSM) that renders an image boundary with center C and a notch P is provided, the method comprising: acquiring at least two frames by the endoscopic camera, having the rigid endoscope in different positions with respect to the camera-head, and detecting boundary centers $C_i$ and notches $P_i$ for each frame; estimating a rotation center $\hat{Q}$ using the detected boundary centers $C_i$ and/or notches $P_i$; estimating a rotation center Q according to the normalized rotation center $\dot{Q}$, boundary centers $C_i$ and notches $P_i$; and comparing the two rotation centers $\hat{Q}$ and Q and deciding about the existence of an anomaly.

In an embodiment of the fifth aspect, the endoscopic lens descriptor $\dot{\Phi}$ is obtained by loading information into the CCU from a database or using QR codes, USB flash drives, manual insertion, engravings in the FSM, RFID tags, an internet connection, etc.

In an embodiment of the fifth aspect, the comparison between the two rotation centers $\hat{Q}$ and Q and the decision about the existence of an anomaly are performed by making use of one or more of algebraic functions, classification schemes, statistical models, machine learning algorithms, thresholding, or data mining.

In an embodiment of the fifth aspect, comparing the boundaries detected at calibration time and during operation for identifying the cause of the anomaly.

In an embodiment of the fifth aspect, the method further comprises providing an alert message to the user, wherein the cause of the anomaly, whether it is a mismatch between the lens in use and the considered calibration or a physical problem with the rigid endoscope and/or the camera-head, is identified.

In a sixth aspect of the present disclosure, a method for detecting an image boundary with center C and a notch P in a frame acquired by using a rigid endoscope that has a Field Stop Mask (FSM) that induces the image boundary with center C and the notch P is provided, the method comprising: using an initial estimation of the boundary with center C and notch P for rendering a ring image, which is an image obtained by interpolating and concatenating image signals extracted from the acquired frame at concentric circles centered in C, wherein the notch P is mapped to the center of the ring image; detecting salient points in the ring image; repeating the following until the detected salient points are collinear; mapping the salient points into the space of the acquired frame and fitting a circle with center C to the mapped points; rendering a new ring image by making use of the fitted circle; detecting salient points in the new ring image; and detecting the notch P in the final ring image using correlation with a known template.

In an embodiment of the sixth aspect, the FSM contains more than one notch, all having different shapes and/or sizes so that they can be identified, in which case the template comprises a combination of notches whose relative location is known.

In an embodiment of the sixth aspect, the notches can have any desired shape.

In an embodiment of the sixth aspect, the notch that is mapped in the center of the ring image is an arbitrary notch.

In an embodiment of the sixth aspect, the initial estimation of the boundary with center C and notch P can be obtained from a multitude of methods which include, but are not limited to, deep/machine learning, image processing, statistical-based and random approaches.

In an embodiment of the sixth aspect, a generic conic is fitted to the mapped points.

In an embodiment of the sixth aspect, the detected center C and/or notch P are used for the estimation of the angular displacement of the rigid endoscope with respect to a camera-head it is mounted on.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure. All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

The described embodiments are to be considered in all respects only as illustrative and not restrictive and the scope of the presently disclosed embodiments is, therefore, indicated by the appended claims rather than by the foregoing description. All changes which come within the meaning and range of equivalency of the claims are to be embraced within their scope. Skilled artisans may implement the described functionality in varying ways for each particular application, but such implementation decisions should not be interpreted as causing a departure from the scope of the disclosed systems and/or methods.

REFERENCES

All of the references cited are expressly incorporated herein by reference. The discussion of any reference is not an admission that it is prior art to the presently disclosed embodiments, especially any reference that may have a publication date after the priority date of this application.

[1] T. Yamaguchi, M. Nakamoto, Y. Sato, K. Konishi, M. Hashizume, N. Sugano, H. Yoshikawa, and S. Tamura, "Development of a camera model and calibration procedure for oblique-viewing endoscopes," Computer Aided Surgery, vol. 9, no. 5, pp. 203-214, February 2004.

[2] C. Wu, B. Jaramaz, and S. Narasimhan, "A full geometric and photometric calibration method for oblique-viewing endoscopes," Computer Aided Surgery, vol. 15, no. 1-3, pp. 19-31, April 2010.

What is claimed is:

1. A method for obtaining a lens descriptor for a rigid endoscope with a Field Stop Mask (FSM), the method comprising:
with the rigid endoscope installed in a characterization camera including the rigid endoscope and a camera head:
acquiring, using the characterization camera, K calibration images at N angular positions between the rigid endoscope and the camera head;
estimating first calibration parameters of the characterization camera at a reference angular position; and
determining the lens descriptor for the rigid endoscope based on the first calibration parameters estimated for the characterization camera at the reference angular position, wherein the lens descriptor includes second calibration parameters different from the first calibration parameters; and
with the rigid endoscope installed in an endoscopic camera different from the characterization camera, calibrating the endoscopic camera using the second calibration parameters contained in the lens descriptor for the rigid endoscope.

2. The method of claim 1, further comprising computing a normalized focal length $\hat{f}$ from $\hat{f}=f/r$, with r being a distance between center $C_0=[C_x, C_y, 1]^T$ and notch $P_0$, and obtaining a normalized principal point $\dot{O}$ and a normalized rotation center $\dot{Q}$ by computing $\dot{O}=AO$ and $\dot{Q}=AQ$, respectively, with A=

$$A = \begin{bmatrix} \cos\beta & -\sin\beta & -C_x\cos\beta + C_y\sin\beta \\ \sin\beta & \cos\beta & -C_x\sin\beta + C_y\cos\beta \\ 0 & 0 & r \end{bmatrix}$$

and β being an angle between line $\overline{CP}$ and a down direction.

3. The method of claim 1, further comprising calibrating the endoscopic camera by:
acquiring an image frame i with the endoscopic camera;
detecting a boundary center $C_i$ and a notch $P_i$ in the image frame i; and
estimating a focal length f, a rotation center Q, and a principal point O according to the boundary center $C_i$, the notch $P_i$, and the second calibration parameters contained in the lens descriptor for the rigid endoscope, wherein the second calibration parameters include a normalized focal length $\hat{f}$, a normalized principal point $\dot{O}$, and a normalized rotation center $\dot{Q}$.

4. The method of claim 3, further comprising determining a radius r of the image frame.

5. The method of claim 4, wherein the focal length f, the principal point O and the rotation center Q are computed by $f=r\hat{f}$, $O=B\dot{O}$ and $Q=B\dot{Q}$, respectively, with B=

$$\begin{bmatrix} r\cos\alpha & r\sin\alpha & C_x \\ -r\sin\alpha & r\cos\alpha & C_y \\ 0 & 0 & 1 \end{bmatrix}$$

and α being the angle between line $\|\overline{C_iP_i}\|$ and the down direction.

6. The method of claim 3, wherein the lens descriptor is obtained by one or more of:
loading information into a camera control unit (CCU) from a database;
reading a QR code;
obtaining information from a USB flash drive;
receiving manual input of information from a user;
reading engravings in the FSM;
obtaining information from an RFID tag; or
obtaining information over an internet connection.

7. The method of claim 3, wherein frame i comprises two or more frames, wherein the rotation center Q is determined using one or more of:
three or more boundary centers $C_i$;
three or more notches $P_i$; or
at least one boundary center $C_i$ and at least one notch $P_i$.

8. The method of claim 1, wherein estimating the first calibration parameters includes estimating the first calibration parameters based on rotation of a principal point O around a rotation center Q in the K calibration images.

9. The method of claim 8, wherein the first calibration parameters include a focal length f, a distortion ξ, a principal point $O_0$, and a rotation center Q of the characterization camera at the reference angular position.

10. The method of claim 9, wherein the second calibration parameters contained in the lens descriptor include a normalized focal length $\hat{f}$, a distortion ξ, a normalized principal point $\dot{O}$, and a normalized rotation center $\dot{Q}$.

11. The method of claim 10, further comprising detecting a boundary with a center $C_0$ and a notch $P_0$ at the reference angular position, wherein determining the lens descriptor includes determining the normalized focal length $\hat{f}$, the distortion ξ, the normalized principal point $\dot{O}$, and the normalized rotation center $\dot{Q}$ using the center $C_0$, the notch $P_0$, the focal length f, the principal point $O_0$, and the rotation center Q.

12. The method of claim 1, wherein calibrating the endoscopic camera includes calibrating the endoscopic camera at least one of (i) at the reference angular position and (ii) in accordance with rotation of the rigid endoscope.

* * * * *